United States Patent [19]

Fujii et al.

[11] Patent Number: 4,646,748
[45] Date of Patent: Mar. 3, 1987

[54] ULTRASONIC MEASUREMENT METHOD, AND APPARATUS THEREFOR

[75] Inventors: Tadashi Fujii, Fujinomiya; Yoshizo Ishizuka, Fuji, both of Japan

[73] Assignee: Terumo Kabushiki Kaisha, Tokyo, Japan

[21] Appl. No.: 702,829

[22] Filed: Feb. 19, 1985

[30] Foreign Application Priority Data

Feb. 23, 1984 [JP] Japan .................................. 59-31516

[51] Int. Cl.$^4$ .............................................. A61B 10/00
[52] U.S. Cl. ........................................ 128/660; 73/599
[58] Field of Search ................... 128/660-663; 73/599

[56] References Cited

U.S. PATENT DOCUMENTS

| | | | |
|---|---|---|---|
| 4,174,635 | 11/1979 | Oldendorf | 73/606 |
| 4,176,658 | 12/1979 | Kossoff et al. | 128/660 |
| 4,228,804 | 10/1980 | Holasek et al. | 128/660 |
| 4,389,893 | 6/1983 | Ophir et al. | 73/599 |
| 4,452,082 | 6/1984 | Miwa | 73/599 |
| 4,511,984 | 4/1985 | Sumino et al. | 128/660 X |

FOREIGN PATENT DOCUMENTS 0041403 12/1981 European Pat. Off. .
0043158 1/1982 European Pat. Off. .
0091768 10/1983 European Pat. Off. .

OTHER PUBLICATIONS

Journal of the Acoustical Society of America, vol. 69, No. 6, Jun. 1981, pp. 1838-1840, "Multifrequency Echoscopy for Quantitative Acoustical Characterization of Living Tissues" Y. Hayakawa et al.

IEEE Transactions on Acoustics, Speech and Signal Processing, vol. ASSP-32, No. 1, Feb. 1984, pp. 1-6, "Estimating Acoustic Attenuation from Reflected Ultrasound Signals; Comparison of Spectral-shift and Spectral-difference Approaches" R. Kuc.

Primary Examiner—Kyle L. Howell
Assistant Examiner—Francis J. Jaworski
Attorney, Agent, or Firm—Frishauf, Holtz, Goodman & Woodward

[57] ABSTRACT

In a method and apparatus for ultrasonic measurement, an ultrasonic pulse is transmitted into a object and received as an echo signal following reflection within the object, and the acoustic characteristic of the object is measured based on object position and frequency information contained in the echo signal. The measured acoustic characteristic is representative of information relating to degree of attenuation and frequency dependence thereof inside the object and obtained from the position and frequency information contained in the echo signal. The apparatus according to this invention displays an image of the distribution of the object acoustic characteristic obtained from the measured acoustic characteristic.

12 Claims, 31 Drawing Figures

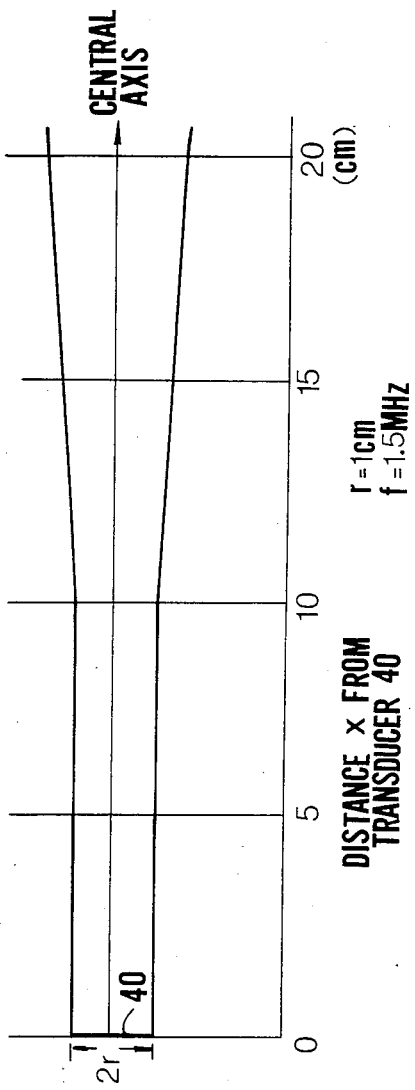

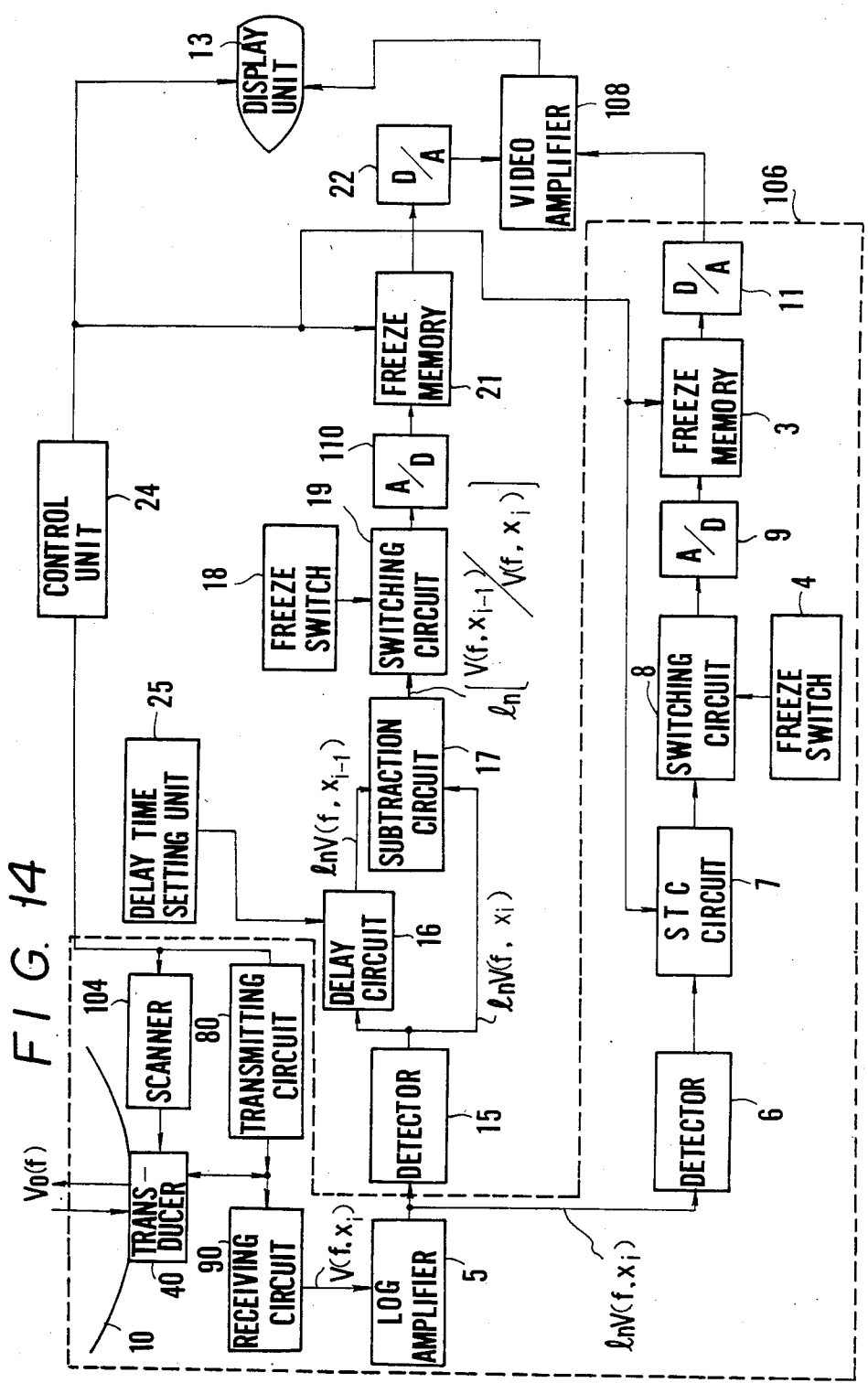
F I G. 14

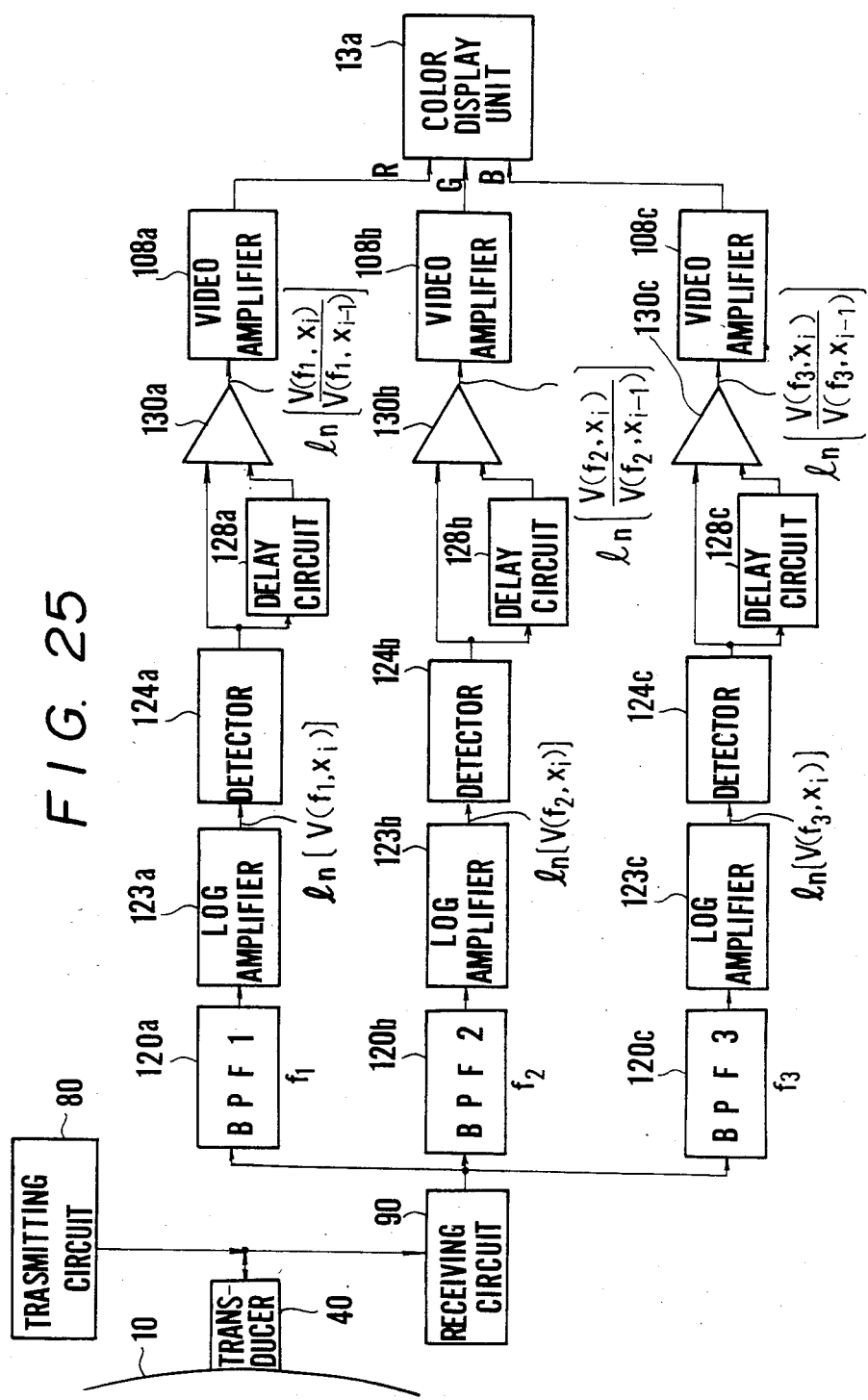

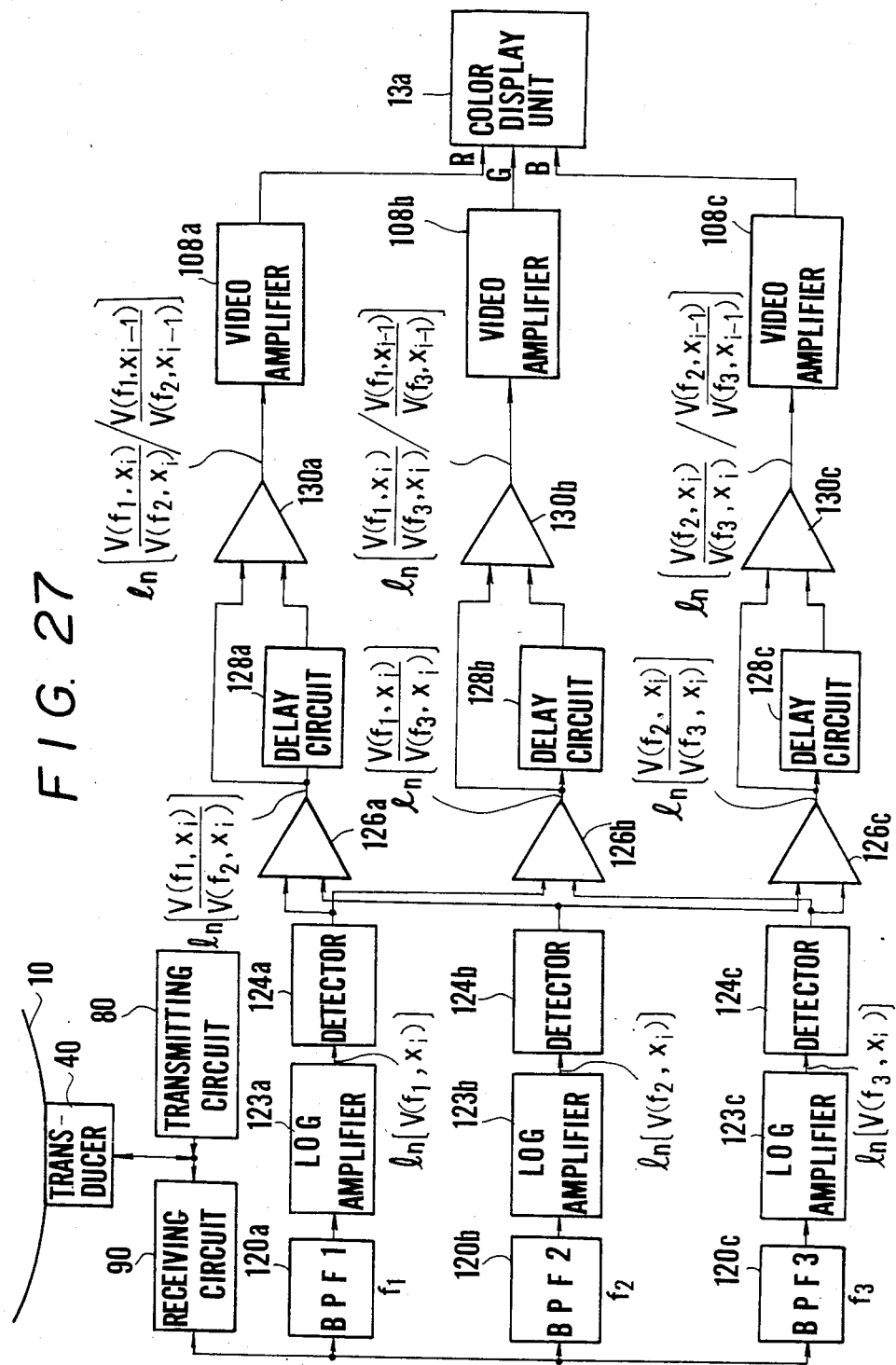

ULTRASONIC MEASUREMENT METHOD, AND APPARATUS THEREFOR

BACKGROUND OF THE INVENTION

1. Field of the Invention

This invention relates to improvements in an ultrasonic measurement method and apparatus for subjecting an object to an ultrasonic transmission, and receiving reflected ultrasonic waves from the interior of the object to measure the acoustic characteristics of the interior. More particularly, the invention relates to an ultrasonic measurement method and apparatus for providing information relating to the frequency dependence of ultrasonic attenuation within the object.

2. Description of the Prior Art

Ultrasonic measurement techniques find application widely in such fields as material testing, sonar and medical diagnosis. In particular, ultrasound scanner systems for medical purposes have recently been developed.

The principle of operation of an ultrasound scanner system resides in use of a pulse-echo method and utilizes a phenomenon wherein an ultrasonic pulse transmitted into a living body, which is the object undergoing measurement, is reflected at a boundary where there is a difference in acoustic impedance in living tissue. The reflected wave (echo) is received and processed to display a tomograph of the living body by a so-called B-mode method. The echo therefore contains information relating to the scattering and reflection characteristic of the region where the echo is produced and the round-trip attenuation characteristic along the propagation path, as well as such information as the degree of ultrasonic attenuation, acoustic impedance and propagation velocity of sound, all in living tissue. Despite such a variety of effective information contained in the echo, however, the information being utilized at the present time is solely the amplitude of the echo.

More specifically, in the present state of the art, the propagation velocity of sound in living tissue is assumed to be constant and, with regard to attenuation ascribable to ultrasonic propagation, the value of the echo amplitude obtained by an arbitrary correction performed by a so-called STC (sensitivity time control) circuit is displayed as a mere tomograph on a cathode-ray tube following brightness modulation. This is referred to as a "B-mode display". Accordingly, the tomograph obtained is nothing more than a qualitatively imaged two-dimensional distribution at acoustic impedance boundaries in living tissue, so that morphological information relating to the position and shape of the biological tissue inevitably forms the core of the information utilized. However, the state of the art is such that biological tissue characteristics such as degree of attenuation and propagation velocity of sound are not measured.

Several attempts at attaining attenuation information relating to biological tissue have been reported. However, as will be described below in further detail, an echo signal contains two types of information, namely attenuation due to propagation through biological tissue, and intensity of reflection at an interface or boundary where there is a difference in acoustic impedance. Both of these quantities are unknown. Therefore, isolating the effects of these two quantities is extremely difficult at the present time.

If the reflected intensity is assumed to be independent of the frequency of the ultrasonic waves and ultrasonic waves having two or more frequencies are transmitted and the ultrasonic echo is received with regard to the same portion of the object under measurement followed by measuring the sound pressure ratio of each frequency component of the echo, then it will be possible to eliminate the influence of the reflected intensity and derive an attenuation coefficient. See the specification of Japanese Patent Application Laid-Open No. 49-38490 in this connection. The foregoing assumption holds in the case of an acoustic interface having a sufficiently wide spread in comparison with the wavelength of the ultrasonic waves, e.g. in the case of a planar reflector. With actual biological tissue, however, scatterers of a size approximately equivalent to or smaller than the wavelengths used are also considered to be present. Therefore, the foregoing assumption will not necessarily hold true for the entirety of a biological tissue.

If it is assumed that the reflected intensity is approximately constant at a certain portion of a biological tissue, then one may consider that the echo sound pressure ratio across the front and back of this portion of the tissue is proportional to the attenuation coefficient. Further, several theories have been brought forward wherein an attenuation coefficient is obtained by presupposing a function for the frequency dependence of the reflected intensity, transmitting ultrasonic waves having three or more frequencies, receiving the ultrasonic echos from the same portion of the object under measurement, and measuring the sound pressure of each frequency component of the echos, with the attenuation coefficient being obtained from the sound pressure. See the specification of Japanese Patent Application Laid-Open No. 56-147082.

Thus, the method employed to isolate and measure an attenuation coefficient in all of the foregoing cases involves making an assumption with regard to the reflected intensity, as well as transmitting and receiving ultrasonic waves having a single frequency component or a plurality of frequency components.

Several attempts to measure degree of attenuation combining attenuation and reflection (scattering information have been reported (Japanese Patent Application Laid-Open Nos. 58-24824 and 57-179745), and there have been reports of attempts to measure the frequency dependence of the degree of attenuation (Japanese Patent Application Laid-Open Nos. 57-89858, 57-139326, 57-209040). Basically, these reports disclose performing frequency analysis by well-known Fourier analysis or the like with regard to an echo waveform (signal) at a region of interest in biological tissue, and displaying the obtained frequency spectrum together with the conventional tomograph. These approaches display a difference between spectra at two points in the region of interest to obtain information relating to the frequency dependence of the acoustic characteristic (attenuation) in the region of interest. In any case, the items of information obtained are spectra and the diagnosis of tissue properties is performed by ascertaining any change in the shape of the spectra themselves in comparison with image information, namely the conventional tomograph. Performing diagnosis in such fashion involves numerous problems in actual practice. Moreover, one can conjecture that problems will also be encountered in ascertaining in real-time the distribution of a spectrum with respect to the spread of the tissue.

A well-known method of displaying tomographs of different frequencies obtained by multifrequency tomography is referred to as the "Spectra Color" method. The details of this method are reported in "Imaging of Invisible Information" compiled by the Institute of Television Engineers of Japan, pp. 195-196, published by Shokodo K.K., in Lecture Discourses 28-27 (pp. 47-48) of the 28th meeting (November, 1975) of the Japan Society of Ultrasonics in Medicine, and in the specification of U.S. Pat. No. 4,228,804. Though these methods attempt to ascertain the frequency dependence of biological tissue attenuation information by using different frequencies, they do nothing more than provide a superimposed display of the tomographs for the respective frequencies used. Accordingly, a fundamental problem encountered with these methods is the fact that a tissue which by nature has a certain attenuation with respect to ultrasonic waves exhibits a measured attenuation value which is different owing to the thickness of the attenuating medium (tissue), the distance from the ultrasonic transducer to the medium (tissue) to be examined, and the influence of other tissues lying between the transducer and the tissue to be examined.

SUMMARY OF THE INVENTION

An object of the present invention is to provide an image of heretofore unobtainable information relating to attenuation in biological tissue by treating attenuation and reflection (scattering) in combination as the degree of attenuation in the biological tissue rather than isolating attenuation and reflection (scattering) on the basis of presuppositions, and both measuring and imaging in real-time the frequency dependence of the degree of attenuation.

According to one aspect of the present invention, the foregoing object is attained by providing an ultrasonic measurement method for measuring an acoustic characteristic of an object under examination by transmitting an ultrasonic pulse into the object and detecting an ultrasonic echo signal reflected from within the object. The method includes an ultrasonic transceiving step of transmitting ultrasonic pulses into the object and obtaining ultrasonic echo signals, reflected from within the object, that will have a desired frequency band, and a measurement step of discriminating echo signals regarding a desired region of interest inside the object from the echo signals obtained in the transceiving step, and measuring the acoustic characteristic of the region of interest on the basis of the discriminated echo signals.

The ultrasonic transceiving step includes a transmitting step of transmitting ultrasonic pulses over a wide band, and a receiving step of receiving ultrasonic echo signals over a wide band from the object and discriminating them according to a single desired frequency band or a plurality of desired frequency bands.

The acoustic characteristic is an attenuation coefficient inclusive of an ultrasonic absorption coefficient, a reflection scattering coefficient and a transmission scattering coefficient.

The measurement step comprises calculating the attenuation coefficient of the region of interest based on an echo signal ratio in a desired frequency band measured with respect to two boundaries in the region of interest.

The measurement step comprises calculating the frequency dependence of the attenuation coefficient of the region of interest based on an echo signal ratio in a plurality of desired frequency bands measured with respect to two boundaries in the region of interest.

The ultrasonic transceiving step comprises transmitting ultrasonic pulses into, and receiving ultrasonic pulses from, the object in such a manner that echo signal trains from the region of interest of the object are formed substantially of a plurality of scanning lines, and the measurement step comprises measuring an acoustic characteristic which is composed of mean values formed over predetermined sets of scanning lines of the plurality of scanning lines.

According to another aspect of the present invention, the foregoing object is attained by providing an ultrasonic measurement apparatus for measuring an acoustic characteristic of an object under examination by transmitting an ultrasonic pulse into the object and detecting an ultrasonic echo signal reflected from within the object. The apparatus comprises ultrasonic transceiving means for transmitting ultrasonic pulses into the object and obtaining ultrasonic echo signals, reflected from within the object, that will have a desired frequency band, measuring means for discriminating echo signals regarding a desired region of interest inside the object from the echo signals obtained by the ultrasonic transceiving means, and for measuring the acoustic characteristic of the region of interest on the basis of the discriminated echo signals, and display means for displaying the measured acoustic characteristic as a visible image corresponding to the region of interest.

The ultrasonic transceiving means comprises transmitting means for transmitting ultrasonic pulses over a wide band, and receiving means for receiving ultrasonic echo signals over a wide band from the object, the receiving means having a band-pass circuit for passing echo signals of a single desired frequency band or of a plurality of desired frequency bands.

The acoustic characteristic is an attenuation coefficient inclusive of an ultrasonic absorption coefficient, a reflection-scattering coefficient and a transmission-scattering coefficient.

The measurement means has means for calculating the attenuation coefficient of the region of interest based on an echo signal ratio, in a single desired frequency band or in a plurality of desired frequency bands, measured with respect to two boundaries in the region of interest.

The measurement means has means for calculating frequency dependence of the attenuation coefficient of the region of interest based on an echo signal ratio, in a plurality of desired frequency bands, measured with respect to two boundaries in the region of interest.

The ultrasonic transceiving means has means for transmitting ultrasonic pulses into, and receiving ultrasonic pulses from, the object in such a manner that the visible image displayed by the display means is formed substantially of a plurality of scanning lines, and the measuring means has means for measuring an acoustic characteristic which is composed of mean values over predetermined numbers of scanning lines of said plurality of scanning lines.

The display means displays an attenuation coefficient in the desired frequency band in a desired color corresponding thereto.

The display means displays frequency dependence of an attenuation coefficient in a desired color corresponding thereto.

The display means has means for adding an attenuation coefficient in the desired frequency band and a high-frequency band signal produced by the band-pass circuit in said desired frequency band.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

FIGS. 1 through 3 are views useful in describing the fundamental principle of the present invention, in which FIGS. 2 and 3 are graphical representations;

FIGS. 5 through 8 are views useful in describing the ultrasonic measurement method of the present invention with regard to a simple model, in which FIGS. 6 through 8 are graphical representations;

FIG. 14 is a block diagram illustrating an embodiment of an ultrasonic measurement apparatus according to the present invention;

FIGS. 15 through 17 are block diagrams illustrating partial modifications in the embodiment of FIG. 14;

FIGS. 21, 22, 24, 25 and 27 through 29 are block diagrams illustrating other embodiments of the present invention.

DESCRIPTION OF THE PREFERRED EMBODIMENT

Figure 1:
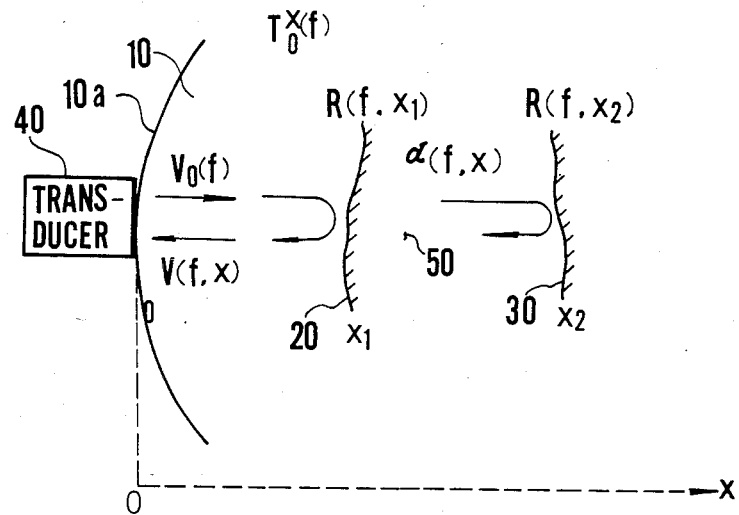

The principle of the present invention will be described with reference to FIG. 1.

Let $V_o(f)$ represent the amplitude of an ultrasonic pulse transmitted into an object 10 from an ultrasonic transducer 40, where f stands for the frequency of the ultrasonic wave. The following equation gives the amplitude $V(f,x_1)$ of an echo signal from a surface 20 at which the acoustic impedance inside the object 10 is discontinuous (where $x=x_1$ is the distance from the surface 10a of the object 10 to the surface 20):

$$V(f, x_1) = V_o(f) \cdot T_o^{x1}(f) \cdot R(f, x_1) \cdot \qquad (1)$$

$$T_{x1}^o(f) \cdot \exp\left(-2 \int_o^{x_1} \alpha(f, x)dx\right)$$

In Eq. (1), $R(f,x_1)$ represents a reflection coefficient, $T_o^{x1}(f)$ the product of transmission coefficients along the propagation path of the ultrasonic wave from the object surface ($x=0$) to the discontinuity surface 20 ($x=x1$), and $T_{x1}^o(f)$ a value which is the inverse of the above product, namely the product of transmission coefficients from $x=x_1$ to $x=0$. Several surfaces of acoustic discontinuity may be considered to reside between the discontinuity surface 20 and the object surface. Further, $\alpha(f,x)$ represents an absorption coefficient.

Taking the natural logarithm of both sides of Eq. (1) and transforming gives the following equation:

$$\ln[V(f, x_1)/V_o(f)] = \ln[T_o^{x1}(f) \cdot T_{x1}^o(f)] + \qquad (2)$$

$$\ln[R(f, x_1)] - 2 \int_o^{x_1} \alpha(f, x)dx$$

We may obtain an equation similar to Eq. (1) with respect to a surface of discontinuity 30 within the same object:

$$\ln[V(f, x_2)/V_o(f)] = \ln[T_o^{x2}(f) \cdot T_{x2}^o(f)] + \qquad (3)$$

$$\ln[R(f, x_2)] - 2 \int_o^{x_2} \alpha(f, x)dx$$

Subtracting Eq. (3) from Eq. (2) results in the following equation:

$$\ln[V(f, x_1)/V(f, x_2)] = \ln[1/(T_{x1}^{x2}(f) \cdot T_{x2}^{x1}(f)] + \qquad (4)$$

$$\ln[R(f, x_1)/R(f, x_2)] + 2 \int_{x_1}^{x_2} \alpha(f, x)dx$$

$$(\because T_o^{x2}(f) = T_o^{x1}(f) \cdot T_{x1}^{x2}(f), T_{x2}^o = T_{x2}^{x1}(f) \cdot T_{x1}^o(f))$$

The significance of Eq. (4) is that $\ln[V(f,x_1)/V(f,x_2)]$, which is the natural logarithm of the ratio of the amplitudes of the echos from the two discontinuity surfaces 20, 30, contains the following information: the value of the integral $$\int_{x_1}^{x_2} \alpha(f, x)dx$$

of the absorption coefficients in a region 50 between the surfaces 20 and 30, the value of the natural logarithm $\ln[R(f,x_1)/R(f,x_2)]$ of the ratio of the reflection coefficients at the surfaces 20 and 30, and a value $\ln[1/(T_{x1}^{x2}(f) \cdot T_{x2}^{x1}(f)]$ relating to the transmission coefficients for propagation of ultrasonic waves in the region 50.

Figure 19:
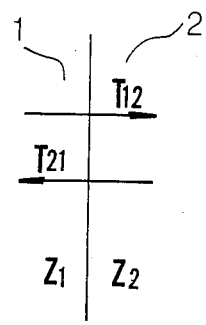
FIGS. 19 and 20 are views useful in describing the principle of the present invention.

Though there is as yet no correct data regarding the transmission coefficient of soft biological tissue, we can take the following approach. Specifically, it is known that the mean acoustic impedence of soft biological tissue is $1.63 \times 10^6$ (kg/m$^2$ s), and that the acoustic impedence ranges roughly between $1.4 \times 10^6$ and $1.7 \times 10^6$ (kg/m$^2$ s). We may investigate the value of the transmission coefficient by using a model of a planar layer. Specifically, as shown in FIG. 19, assume a case in which there are two layers 1 and 2 having respective acoustic impedences $Z_1$ and $Z_2$ the values of which are farthest apart from each other. In such case, the transmission coefficient $T_{12}$ of an ultrasonic wave from layer 1 of acoustic impedence $Z_1$ to layer 2 of acoustic impedence $Z_2$ will be $$T_{12} = \frac{2Z_2}{Z_1 + Z_2}$$

and the transmission coefficient $T_{21}$ of an ultrasonic wave from layer 2 to layer 1 will be $$T_{21} = \frac{2Z_1}{Z_1 + Z_2}$$

$$T_{12} \cdot T_{21} = \frac{4Z_1 Z_2}{(Z_1 + Z_2)^2} + \frac{4\frac{Z_2}{Z_1}}{\left(1 + \frac{Z_2}{Z_1}\right)^2}$$

Figure 20:
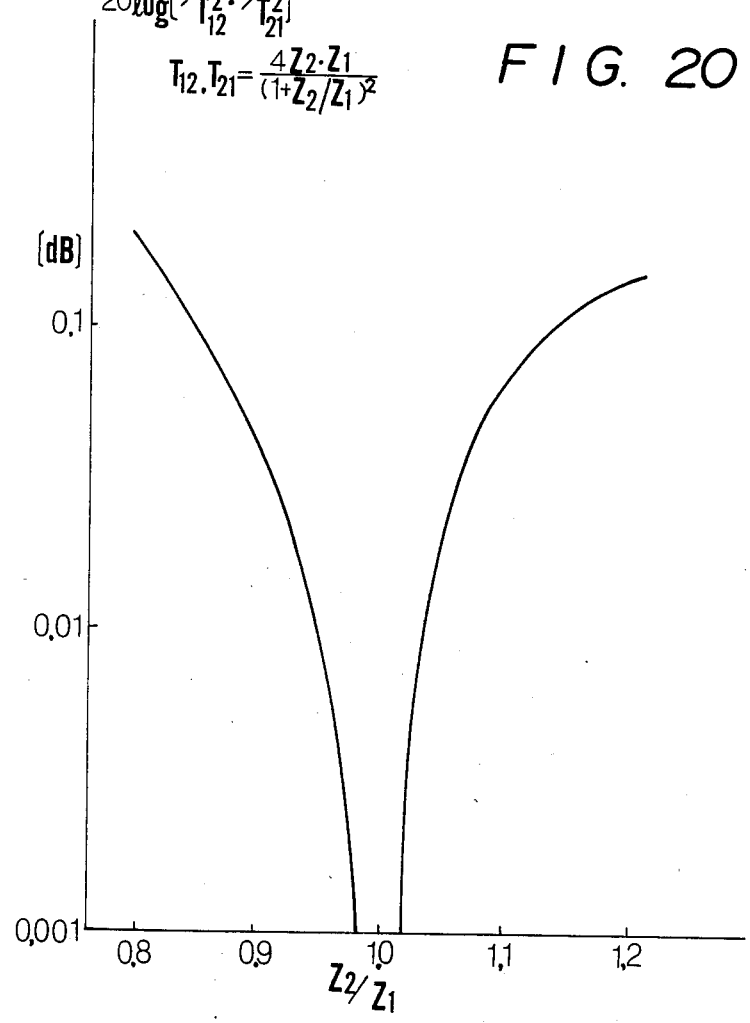

As an example, if we assume that $Z_1=1.4$, $Z_2=1.7$ hold, then we will have $Z_2/Z_1=1.7/1.4=1.214$, $T_{12}=T_{21}=0.991$, $T_{12}^2 \cdot T_{21}^2=0.982$, $\ln[1/T_{12}^2 T_{21}^2]=\ln[1.108]=0.019$. Applying a dB conversion gives us $-0.158$ dB. In actuality, the difference in acoustic impedance may be considered small in terms of mean values. For example, assuming that $Z_1=1.5$, $Z_2=1.6$ hold, we have $Z_2/Z_1=1.06$, so that $\ln[1/(T_{12}^2 \cdot T_{21}^2)]=0.002$. Applying a dB conversion gives 0.018 dB. FIG. 20 shows the result of calculating the relation between $Z_2/Z_1$ and $\ln[1/(T_{12}^2 \cdot T_{21}^2)]$.

Meanwhile, it is known that the absorption coefficient of soft biological tissue ranges roughly between 0.5 and 2.0 dB/cm MHz. The range is from 1.5 to 6.0 dB/cm for 3 MHz, which is the frequency band oridinarily used. Accordingly, if attenuation due to absorption and attenuation due to transmission are compared on a per-centimeter basis, the latter can be considered to be 1/10 to 1/100 the magnitude of the former, or even smaller. If attenuation per millimeter due to absorption is 0.15 to 0.6 dB/mm and the relation $0.86 \leq Z_2/Z_1 \leq 1.17$ holds from FIG. 20, then attenuation due to transmission can be considered to be about 1/10 the absorption coefficient or smaller. Therefore, with respect to soft biological tissue having a mean acoustic impedance of $1.63 \times 10^6$ (kg/m² s), attenuation due to transmission through soft tissue having an acoustic impedance ranging from $1.4 \times 10^6$ to to $1.9 \times 10^6$ (kg/m² s) can be estimated to be about 1/10 of attenuation due to absorption.

A well-defined theory for calculating the actual transmission coefficient of soft biological tissue has not yet been established. However, when the difference in acoustic impedance is considered to be very small, the transmission coefficient can be expected to come quite close to unity and may be assumed to be negligible in comparison with the absorption coefficient. In the event that the transmission coefficient is small but not neglible with respect to the absorption coefficient, then this will appear in the absorption coefficient as an error. Tables I and II indicate values of acoustic impedance and absorption coefficients for biological tissue.

TABLE I

| Biological Tissue | Acoustic Impedance ($\times 10^5$ g/cm² sec) |
|---|---|
| Fat | 1.38 |
| Aqueous humour of eye | 1.50 |
| Vitreous humour of eye | 1.52 |
| Brain | 1.58 |
| Blood | 1.61 |
| Kidney | 1.63 |
| Human tissue (mean value) | |
| Spleen | 1.64 |
| Liver | 1.65 |
| Muscle | 1.70 |
| Lens of eye | 1.84 |
| Skull-bone | 7.80 |

TABLE II

| Tissue | $\alpha/f$ Mean Value (dB/cm MHz) | $\alpha/f$ Standard Deviation (dB/cm MHz) | Frequency Range (MHz) |
|---|---|---|---|
| Aqueous or vitreous humour of eye | 0.10 | — | 6–30 |
| Blood | 0.18 | — | 1.0 |
| Fat | 0.63 | 0.073 | 0.8–7.0 |
| Medulla oblongata along fibers | 0.80 | 0.071 | 1.7–3.4 |
| Brain | 0.85 | 0.056 | 0.9–3.4 |
| Liver | 0.94 | 1.058 | 0.3–3.4 |
| Kidney | 1.0 | 0.04 | 0.3–4.5 |
| Spinal cord | 1.0 | — | 1.0 |
| Medulla oblongata across fibers | 1.2 | 0.05 | 1.7–3.4 |
| Muscle, along fibers | 1.3 | 0.07 | 0.8–4.5 |
| Heart muscle | 1.8 | 0.10 | 0.3–4.5 |
| Lens of eye | 2.0 | — | 3.3–13 |

Solely for the case of soft biological tissue, then, the sum of the reflection and absorption terms may be given as $\ln[V(f,x_1)/V(f,x_2)]$, as shown by the following equation:

$$\ln[V(f, x_1)/V(f, x_2)] = \ln[R(f, x_1)/R(f, x_2)] + 2 \int_{x_1}^{x_2} \alpha(f, x)dx \quad (5)$$

In either Eq. (4) or (5), the observed value $\ln[V(f,x_1)/V(f,x_2)]$ expresses attenuation information (absorption, reflection, transmission) at the frequency f of the ultrasonic wave in the region 50, which lies between the distances $x_2$, $x_1$ from the surface of the object (i.e., $x_2-x_1$). Therefore, let us calculate the degree of attenuation in terms of per-unit length and express such anew by $\beta(f,x)$. We may thus define $\beta(f,x)$ as follows:

$$\beta(f, x) = \frac{1}{x_2 - x_1} \times \ln[V(f, x_1)/V(f, x_2)] \quad (6)$$

It has been reported that according to in-vitro experiments to date, the degree of attenuation in soft biological tissue has a dependence of the first or second power with respect to frequency. In other words, $$\beta(f,x) = \beta_0(x) f^n \quad (n=1-2) \quad (7)$$

In order to measure the frequency dependence of attenuation, it will suffice to evaluate Eq. (5) for two frequencies $f_1$, $f_2$.

$$\ln[V(f_1, x_1)/V(f_1, x_2)] = \quad (8)$$

$$\ln[R(f_1, x_1)/R(f_1, x_2)] + 2 \int_{x_1}^{x_2} \alpha(f_1, x)dx$$

$$\ln[V(f_2, x_1)/V(f_2, x_2)] = \quad (9)$$

$$\ln[R(f_2, x_1)/R(f_2, x_2)] + 2 \int_{x_1}^{x_2} \alpha(f_2, x)dx$$

We arrive at the following equation by subtracting Eq. (9) from Eq. (8), that is, by taking the difference between the observed values for $f_1$ and $f_2$:

$$\ln\left[\frac{V(f_1, x_1)}{V(f_1, x_2)} \bigg/ \frac{V(f_2, x_1)}{V(f_2, x_2)}\right] = \quad (10)$$

$$\ln\left[\frac{R(f_1, x_1)}{R(f_1, x_2)} \bigg/ \frac{R(f_2, x_1)}{R(f_2, x_2)}\right] + 2\int_{x_1}^{x_2}[\alpha(f_1, x) - \alpha(f_2, x)]dx$$

In accordance with the definition of Eq. (6), we arrive at the following:

$$\frac{1}{x_2 - x_1} \cdot \ln\left[\frac{V(f_1, x_1)}{V(f_1, x_2)} \bigg/ \frac{V(f_2, x_1)}{V(f_2, x_2)}\right] = \quad (11)$$

$$\beta(f_1, x) - \beta(f_2, x) = \beta_0(x)[f_1^n - f_2^n]$$

$$\beta_0(x) = \frac{1}{(x_2 - x_1)} \cdot \frac{1}{(f_1^n - f_2^n)} \cdot \quad (12)$$

$$\ln\left[\frac{V(f_1, x_1)}{V(f_1, x_2)} \bigg/ \frac{V(f_2, x_1)}{V(f_2, x_2)}\right]$$

Figure 2:
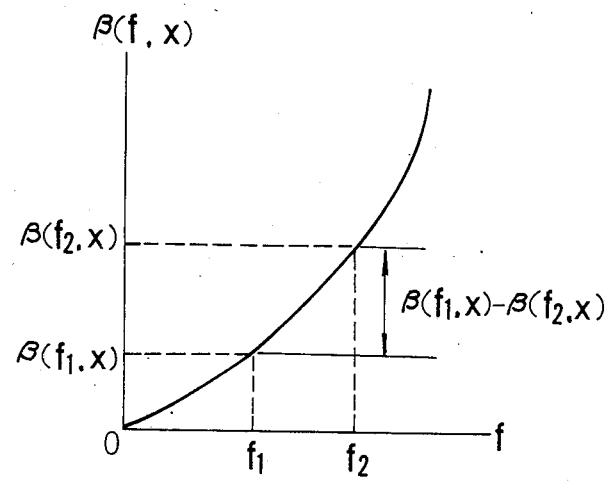

From Eq. (11), it is thus possible to measure the difference between attenuation $\beta(f_1,x)$ which prevails at the frequency $f_1$ and the attenuation $\beta(f_2,x)$ which prevails at the frequency $f_2$, namely the frequency dependence of the degree of attenuation, as shown in FIG. 2.

Figure 3:
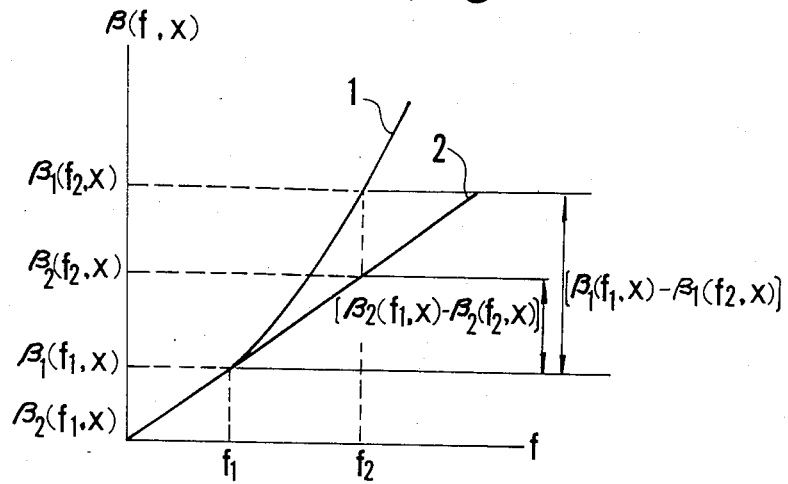

As indicated in Eq. (6), $\beta(f_1, x)$ can be measured by measuring solely the single frequency $f_1$. However, as shown in FIG. 3, if there are attenuation curves 1 and 2 for tissues for which the frequency dependence of attenuation differs, or if the frequency dependence for a certain tissue should change in a manner indicated by the curves 1 and 2 for some reason such as a disease, measuring the frequency dependence will be possible by making use of two or more frequencies and it will be possible to express the difference between tissue 1 and the tissue 2.

Since $\beta(f,x)$ and $[\beta(f_1, x) - \beta(f_2, x)]$ as defined above are items of information indicative of absorption and reflection/scattering in living tissue, let us describe them in connection with their positive, negative and zero values based on the relationship between the two attenuation mechanisms. Let us consider $\beta(f,x)$ first. From $$\beta(f, x) = \frac{1}{x_2 - x_1} \cdot \ln[(V(f, x_1)/V(f, x_2)]$$

we have the following:

$$\beta(f, x) \begin{cases} > 0 \text{ where } V(f, x_1) > V(f, x_2) \\ = 0 \text{ where } V(f, x_1) = V(f, x_2) \\ < 0 \text{ where } V(f, x_1) < V(f, x_2) \end{cases}$$

Analyzing the foregoing based on the relationship between the absorption and reflection/scattering terms results in the following:

$$\beta(f, x) = \frac{1}{x_2 - x_1} \cdot \ln[V(f, x_1)/V(f, x_2)] = \frac{1}{x_2 - x_1} \cdot$$

$$\ln[R(f, x_1)/R(f, x_2)] + \frac{2}{x_2 - x_1} \cdot \int_{x_1}^{x_2} \alpha(f, x)dx$$

If the first term of the above equation is taken as the scattering term, then the second term, which is the absorption term, will always have a positive value. Accordingly, the value of $\beta(f,x)$ is decided by the nature of the reflection/scattering term. Specifically, from the following equation:

$$\ln[R(f, x_1)/R(f, x_2)] \begin{cases} > 0 \text{ where } R(f, x_1) > R(f, x_2) \\ = 0 \text{ where } R(f, x_1) = R(f, x_2) \\ < 0 \text{ where } R(f, x_1) < R(f, x_2) \end{cases}$$

$\beta(f,x) > 0$ holds true for $$R(f, x_1) > R(f, x_2), \text{ or for} \quad (1)$$

$$R(f, x_1) < R(f, x_2) \text{ and} \quad (2)$$

$$2\int_{x_1}^{x_2} \alpha(f, x)dx > |\ln[R(f, x_1)/R(f, x_2)]| \text{ or for}$$

$$R(f, x_1) = R(f, x_2) \text{ and } 2\int_{x_1}^{x_2} \alpha(f, x)dx \neq 0. \quad (3)$$

$\beta(f,x) = 0$ holds true for $$R(f, x_1) < R(f, x_2) \text{ and} \quad (1)$$

$$2\int_{x_1}^{x_2} \alpha(f, x)dx = |\ln[R(f, x_1)/R(f, x_2)]| \text{ or for}$$

$$R(f, x_1) = R(f, x_2) \text{ and } 2\int_{x_1}^{x_2} \alpha(f, x)dx = 0. \quad (2)$$

$\beta(f,x) < 0$ holds true for $$R(f, x_1) < R(f, x_2) \text{ and} \quad (1)$$

$$2\int_{x_1}^{x_2} \alpha(f, x)dx < |\ln[R(f, x_1)/R(f, x_2)]|.$$

More specifically, if $R(f,x_1) < R(f,x_2)$ holds and the absolute value of the reflection/scattering term is greater than the value of the absorption term, $\beta(f,x)$ will have a negative value. When $\beta(f,x)$ is zero, this corresponds to a case where $R(f,x_1) < R(f,x_2)$ holds and the absolute values of the absorption and scattering terms are equal, and to a case where $R(f,x_1) = R(f,x_2)$ holds and there is no absorption term. In the other case, $\beta(f,x)$ is positive. When $R(f,x_1) = R(f,x_2)$ holds where $\beta(f,x)$ is positive, $\beta(f,x)$ expresses a pure absorption value.

Let us now consider the nature of $[\beta(f_1 x) - \beta(f_2, x)]$ in the same fashion.

If $f_1 > f_2$ holds, then $\alpha(f_1,x) > \alpha(f_2,x)$ ordinarily will hold true. Accordingly, for the absorption term we will have $$\int_{x_1}^{x_2} [\alpha(f_1, x) - \alpha(f_2, x)]dx > 0.$$

In other words, the absorption term will be positive. We will therefore have the following:
$[\beta(f_1,x) - \beta(f_2,x)] > 0$ holds for $$\frac{R(f_1, x_1)}{R(f_2, x_1)} \geq \frac{R(f_1, x_2)}{R(f_2, x_2)} \text{ or for} \quad (1)$$

$$\frac{R(f_1, x_1)}{R(f_2, x_1)} < \frac{R(f_1, x_2)}{R(f_2, x_2)} \text{ and} \quad (2)$$

$$\int_{x_1}^{x_2} [\alpha(f_1, x) - \alpha(f_2, x)]dx > \left| \ln\left[ \frac{R(f_1, x_1)}{R(f_2, x_1)} \middle/ \frac{R(f_1, x_2)}{R(f_2, x_2)} \right] \right|$$

$[\beta(f_1,x) - \beta(f_2,x)] = 0$ holds for $$\frac{R(f_1, x_1)}{R(f_2, x_1)} < \frac{R(f_1, x_2)}{R(f_2, x_2)} \text{ and} \quad (1)$$

$$\int_{x_1}^{x_2} [\alpha(f_1, x) - \alpha(f_2, x)]dx = \left| \ln\left[ \frac{R(f_1, x_1)}{R(f_2, x_1)} \middle/ \frac{R(f_1, x_2)}{R(f_2, x_2)} \right] \right|$$

or for $$\frac{R(f_1, x_1)}{R(f_2, x_1)} = \frac{R(f_1, x_2)}{R(f_2, x_2)} \text{ and} \quad \int_{x_1}^{x_2} [\alpha(f_1, x) - \alpha(f_2, x)]dx = 0 \quad (2)$$

$[\beta(f_1,x) - \beta(f_2,x)] = 0$ holds for $$\frac{R(f_1, x_1)}{R(f_2, x_1)} < \frac{R(f_1, x_2)}{R(f_2, x_2)} \text{ and} \quad (1)$$

$$\int_{x_1}^{x_2} [\alpha(f_1, x) - \alpha(f_2, x)]dx < \left| \ln\left[ \frac{R(f_1, x_1)}{R(f_2, x_1)} \middle/ \frac{R(f_1, x_2)}{R(f_2, x_2)} \right] \right|$$

The foregoing shows that the degree of attenuation $\beta(f,x)$ can be measured by taking the difference between echo signals in an ultrasonic propagation interval inside the object, and that the frequency dependence of the degree of attenuation can be measured by measuring $\beta(f,x)$ at two or more frequencies and calculating the difference $[\beta(f_1, x) - \beta(f_2,x)]$ (where two frequencies are used).

Let us now discuss the difference between the foregoing method and the conventional "Spectra Color" method.

Figure 4:
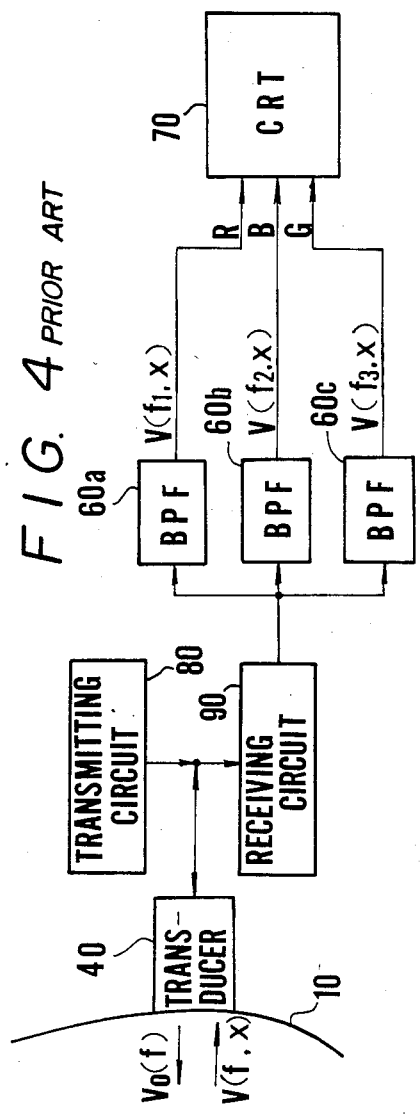
FIG. 4 is a block diagram illustrating an example of an ultrasonic measurement apparatus which operates on the basis of the "Spectra Color" principle according to the prior art.

According to the conventional "Spectra Color" method as described in the specifications of U.S. Pat. No. 4,228,804 and Japanese Utility Model Application Laid-Open No. 58-18507, echo signals over a wide band from a transducer 40, as depicted in FIG. 4, are isolated into three frequency band signals by three band-pass filters (BPF), 60a, 60b, 60c, and the echo signals of the three frequencies are merely displayed in three different colors (red, blue, green) in superimposed form on a color CRT 70. The signals delivered through the band-pass filters 60a, 60b, 60c of center frequency $f(=f_1, f_2, f_3$, respectively) in accordance with this prior-art method can be expressed by the following equations if the terms involving the transmission coefficient are neglected, as set forth above in the discussion of the principle of the present invention:

$$\ln[V(f_1, x)/V_o(f)] = \ln[R(f_1, x)] - 2 \int_0^x \alpha(f_1, x)dx$$

$$\ln[V(f_2, x)/V_o(f)] = \ln[R(f_2, x)] - 2 \int_0^x \alpha(f_2, x)dx$$

$$\ln[V(f_3, x)/V_o(f)] = \ln[R(f_3, x)] - 2 \int_0^x \alpha(f_3, x)dx$$

Here $V_o(f)$ is the amplitude at the time of transmission and is capable of being measured in advance.

Figure 6:
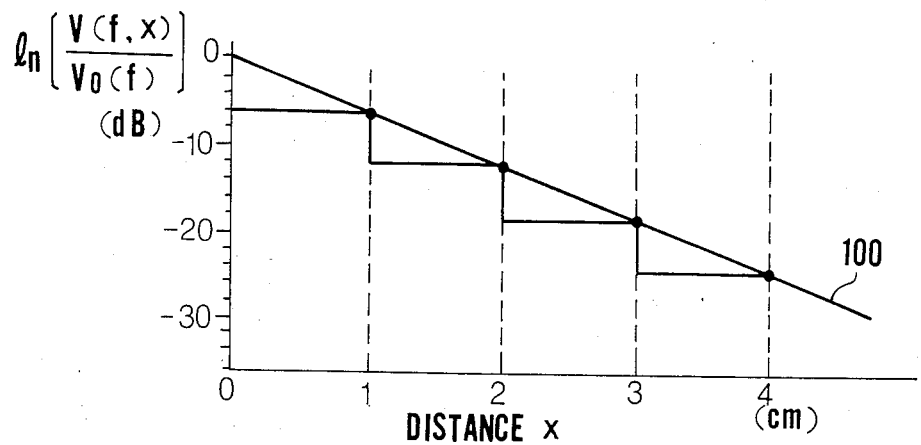
Figure 5:
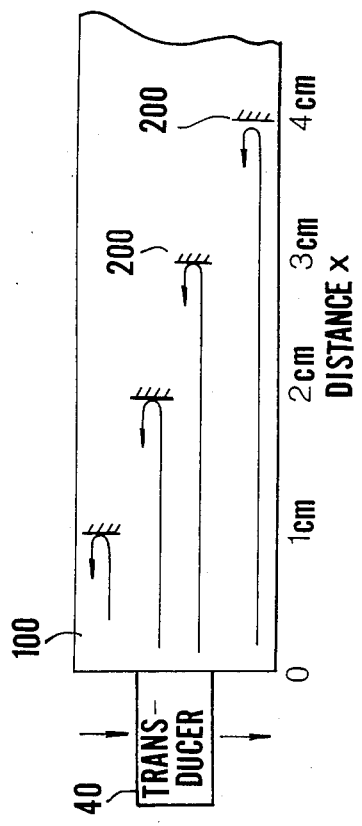

To simplify the discussion, let us consider a system in which reflectors 200 having equal reflection intensities are independently disposed at 1 cm intervals in a medium 100 exhibiting a uniform absorption, as illustrated in FIG. 5. Four echo signals V(f,x) (x=1, 2, 3, 4 cm) reflected from the respective reflectors 200 by scanning the transducer 40 from top to bottom, as indicated by the arrow in FIG. 5, are measured. Assume that the absorption coefficient of the uniform absorption medium 100 is 1 dB/cm MHz, and that the reflection intensity is unity. For a frequency of f=3 MHz, the degree of attenuation will be 3 dB/cm. If we plot the ratio of transmission amplitude $V_o(f)$ to echo signal amplitude V(f,x) along a vertical axis and plot the distance x through the absorption medium 100 along a horizontal axis, the value of $\ln[V(f,x)/V_o(f)]$ from each reflector will be as shown in FIG. 6. Note that the value for x=0 is assumed to be 0 dB. The point marks along the curve 100 are the measured values.

According to the conventional "Spectra Color" method, these values are brightness-modulated as they are for display on the monitor CRT 70. The unfortunate result is that the displayed values diminish in luminance or brightness with distance, as indicated in FIG. 6. The fact that output values are obtained as values which differ from one another when displayed regardless of the perfect uniformity of absorption exhibited by the medium 100 represents a major problem in terms of theory. Such results may be considered to have almost no practical value. Though a method of effecting a correction by using an STC circuit has been reported, the method is an artificial one at best, provides results which are quantitatively poor and lacking in reproducibility, and poses problems entirely the same as those encountered in the conventional ultrasound scanner systems. It is not an exaggeration to say that the results show no improvements whatsoever.

On account of the foregoing theoretical problems encountered in a signal processing method using one frequency (3 MHz in the above description), even a color display using a plurality of frequencies would provide information inadequate quantitatively and in terms of reproducibility.

Let us now describe the present invention. Signal processing already described above in the discussion of the principle of the invention is performed in accordance with the following equation:

$$\ln[V(f, x_1)/V(f, x_2)] = \ln[R(f, x_1)/R(f, x_2)] + 2 \int_{x_1}^{x_2} \alpha(f, x)dx$$

Figure 7:
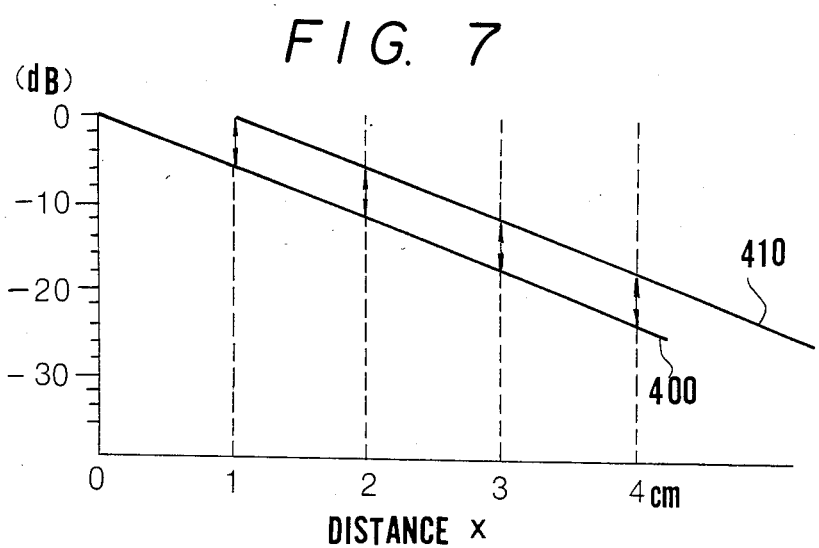
Figure 8:
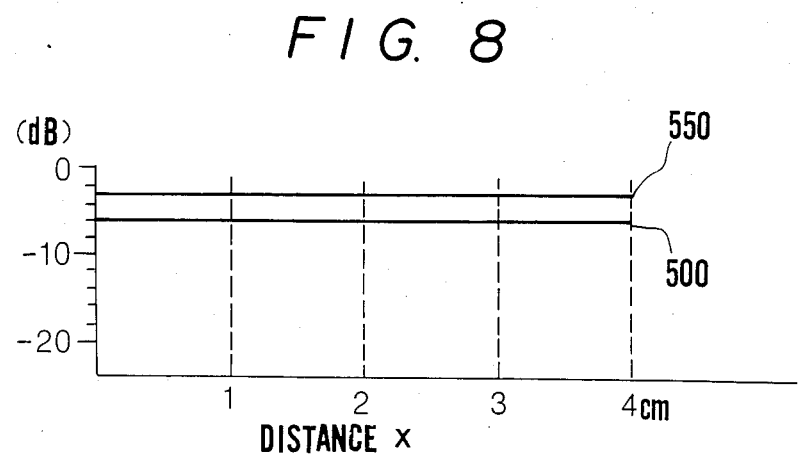

The basic difference between the approach taken by the present invention and the method of the prior art thus resides in employing an arithmetic difference between the values of two echos covering different distances. Let us describe this with reference to FIGS. 7 and 8. A signal 400 is obtained by measurement, followed by producing a signal 410 (by delay circut described later for example), which corresponds to time, 1 cm distant with respect to the signal 400. The difference between the two signals 400, 410 is the waveform 500 depicted in FIG. 8. Taking the difference between the two signals results in an output which is independent of distance, namely an output indicating that the medium is a material for which the attenuation is the same throughout. In terms of the above equation, we may write $$\tfrac{1}{2}\ln[V(f, x_1)/V(f, x_2)] = \int_{x_1}^{x_2} \alpha(f, x)dx$$

from the fact that $R(f,x_1)=R(f,x_2)=1$ holds. In other words, the line 550, which is one-half the value of the waveform 500, affords the absorption coefficient, and it will be apparent from FIG. 8 that this is measured accurately as 3 dB/cm.

Figure 9:
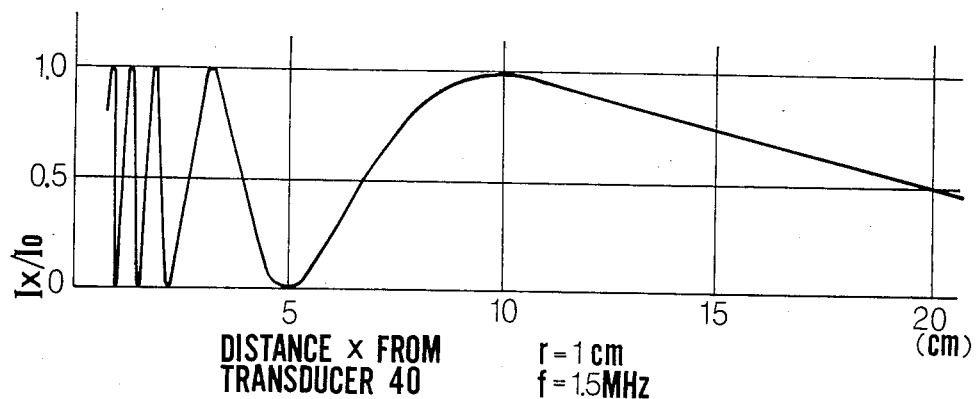
FIGS. 9(a), (b) through 13 are views useful in describing a method of calibrating an ultrasonic transducer used in the apparatus of the present invention.

In actuality, an ultrasonic beam transmitted from the ultrasonic disc transducer 40 toward a substance such as water which attenuates the beam very little develops a difference in sound field owing to the aperture length or the frequency at the center of the transducer. The sound field has the approximate form shown in FIG. 9(a). The intensity of the sound field on the central axis of the transducer 40 varies in accordance with the distance x from the transducer, as illustrated in FIG. 9(b). It should be noted that the vertical axis in FIG. 9(b) indicates the intensity at the distance x with respect to maximum intensity $I_o$.

To make practical use of the apparatus, therefore, a correct measurement cannot be performed unless the apparatus is properly calibrated. To this end, a variation in sound pressure is measured beforehand using a standard medium, and the echo amplitude (sound pressure) from the object under investigation is divided by a standard sound pressure to achieve normalization. This eliminates the influence of the sound field characteristic of the ultrasonic transducer 40 and makes it possible to obtain a more universal value for the measured attenuation.

Figure 10:
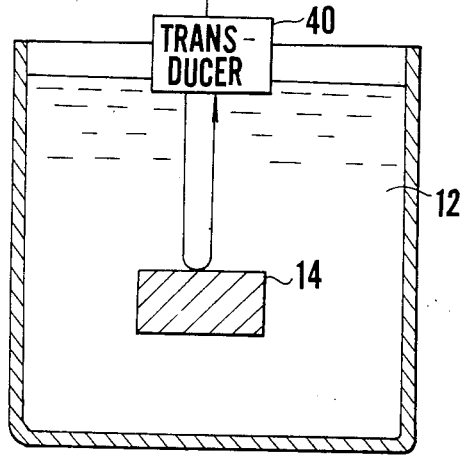
Figure 11:
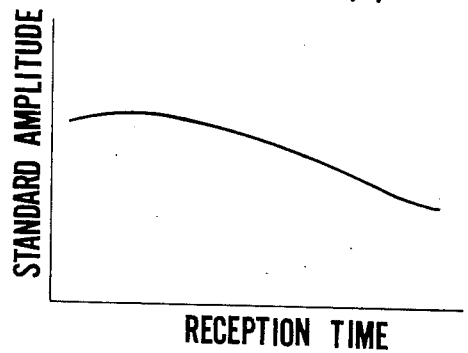

An appropriate method of measurement using a standard medium will now be described with reference to FIG. 10. As shown, a perfect reflector 14 made of stainless steel or the like is submerged in a bath of degassed water 12. The amplitude of an echo received from the perfect reflector 14 serves as a standard sound pressure. A standard sound pressure curve is obtained as shown in FIG. 11 by varying the distance between the ultrasonic transducer 40 and the perfect reflector 14 and measuring the amplitude of the echo received at each distance.

Figure 12:
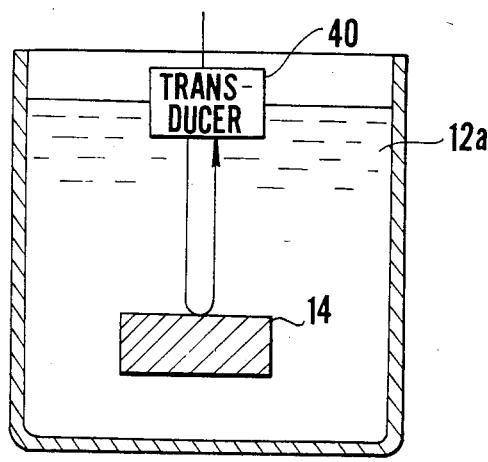

In a more preferred arrangement, a substance such as castor oil 12a, which exhibits an attenuation characteristic substantially equal to that of a living body, is substituted for the degassed water 12, as shown in FIG. 12. When such a medium is used, it is possible to eliminate the influence of a decrease in the mean frequency of the ultrasonic wave owing to attenuation so that a more practical standard sound pressure curve, i.e., one close to that of a living body, can be obtained. However, a number of points are worthy of note. First, it is necessary that the thickness of the perfect reflector 14 be selected in such a manner that echos from the rear and front sides of the reflector 14 do not overlap in terms of time. Second, since the attenuation characteristic of the castor oil 12a exhibits temperature dependence, control of temperature is required. A suitable temperature is between 20° C. and 30° C. to bring the degree of attenuation more or less into conformance with that of a living body.

Figure 13:
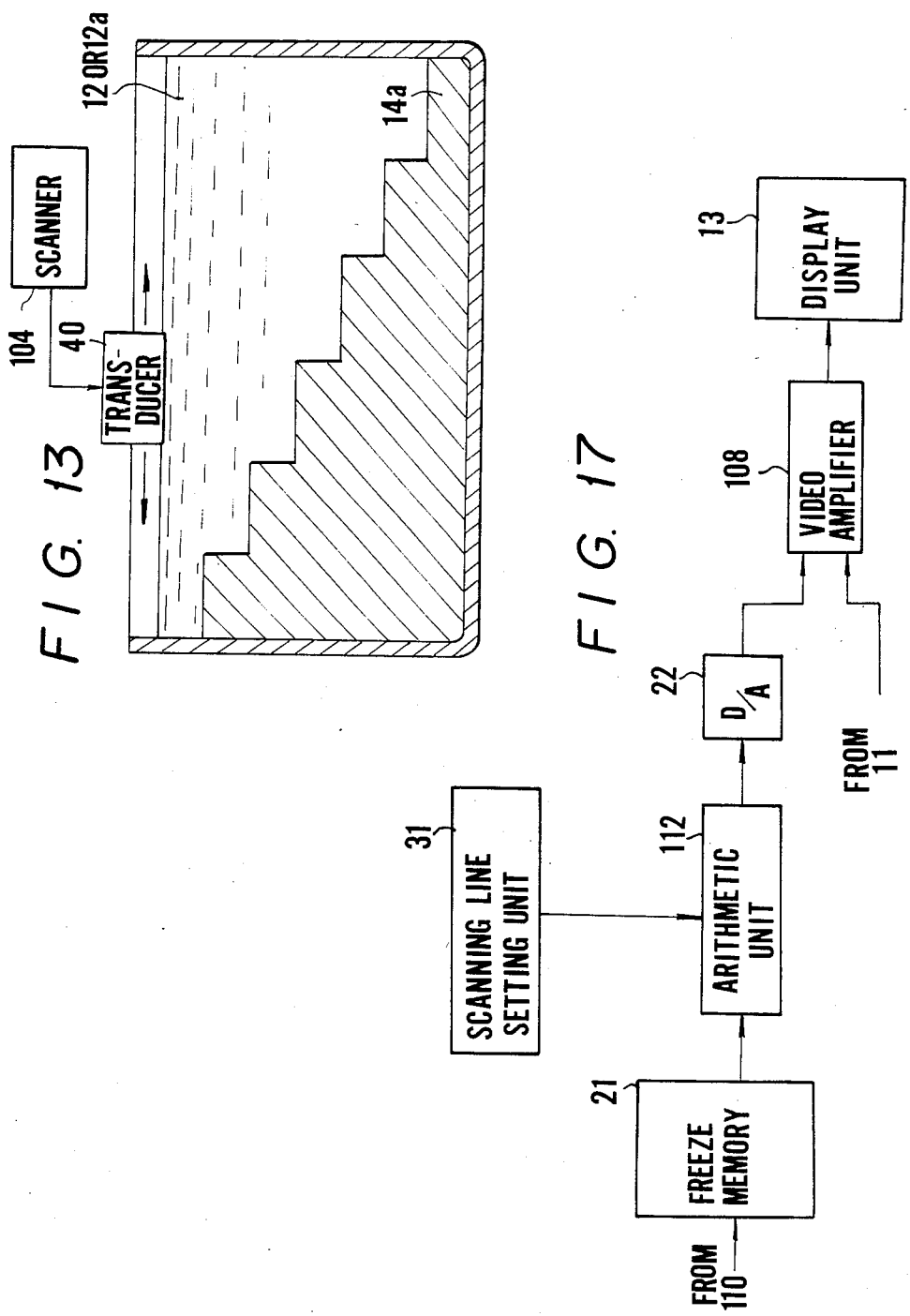

For an apparatus suited to practical use, the standard sound pressure curve would be measured in advance and stored beforehand within the apparatus. If it is desired to remeasure the standard sound pressure curve, the apparatus should be fabricated to include a step-like perfect reflector 14a as shown in FIG. 13. Specifically, if the ultrasonic transducer 40 is arranged so as to be scanned horizontally by a scanner 104, the distance between the ultrasonic transducer 40 and the reflective surface of the reflector 14a can be varied in a stepwise manner. Here the amplitude of the echo from each "step" of the perfect reflector 14a would be measured and the measured amplitudes stored in memory successively to obtain the standard sound pressure curve.

An embodiment of the present invention illustrated in FIG. 14 will now be described in detail.

Figure 15:
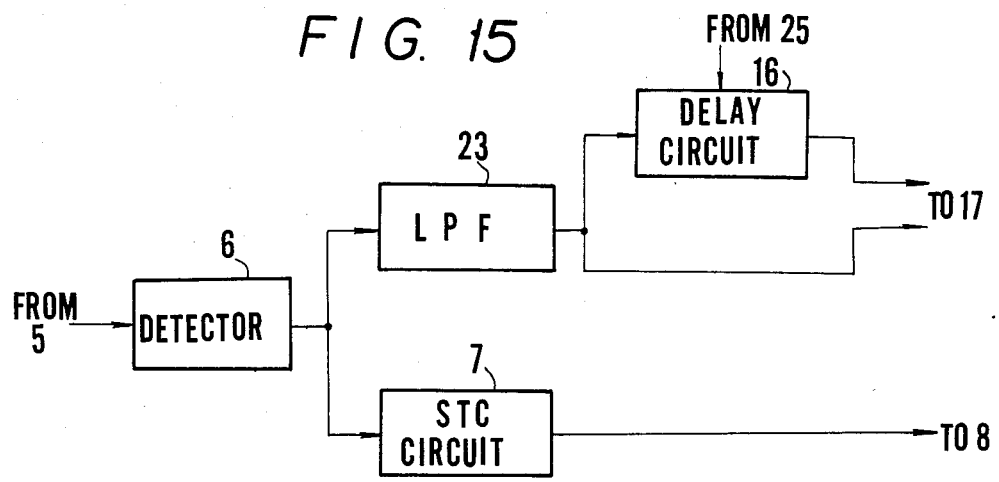

The portion 106 enclosed by the dashed line in FIG. 14 indicates the construction of a conventional B-mode tomographic unit and, being well-known in the art, will not be described in detail here. An echo signal from the object 10 is applied to a detector 15 through a receiving circuit 90 and a logarithmic amplifier (LOG AMPLIFIER) 5. Unlike a detector 6 in the conventional arrangement, the detector 15 also performs the function of a low-pass filter for removing noise and high-frequency components in order to obtain the degree of attenuation correctly. Specifically, the detector 15 is adapted to smoothen the input signal thereto by a detection time constant and pass only a low band component of the signal. It is of course also possible to perform the same function by adopting the arrangement shown in FIG. 15, in which the output of the detector 6 in the prior-art set-up is applied to an STC circuit 7 and also to a low-pass filter 23 (LPF) rather than the filtering circuit 15 of FIG. 14.

The signal delivered by the detector 15 or by the low-pass filter 23 is applied directly to a subtraction circuit 17 as a signal indicative of ln $V(f,x_i)$, and to a subtraction circuit 17 as a signal indicative of ln $V(f,x_{i-1})$ following a time delay effected by a delay circuit 16. The subtraction circuit 17 measures the difference $\{\ln[V(f,x_{i-1})/V(f,x_i)]\}$ between these two signals and produces an output signal indicative of the result. Thereafter, signal processing is the same as in the prior art, with the result of the foregoing being applied to a freeze memory 21 and then subjected to brightness modulation for display in the form of a tomograph on a display unit 13. The time delay of the delay circuit 16 is set by a delay time setting unit 25.

According to this embodiment, the difference signal output of the subtraction circuit 17 is delivered via a switching circuit 19 to an A/D converter 110 where the signal is converted into a digital signal and then stored in the freeze memory 21. The difference signal stored in the freeze memory 21 is read out of the memory under control performed by a control unit 24 and is then converted into an analog signal by a D/A converter 22. A video amplifier 108 subjects the analog signal to brightness modulation for display on the display unit 13, which is a CRT or the like, so that the signal may be displayed in the form of a visible tomograph. To freeze the displayed image, a freeze switch 18 is operated to change over the switching circuit 19, thereby freezing the data which has been stored in the memory 21. The circuit arrangement from the switching circuit 19 onward is substantially the same as that of the conventional portion 106.

Figure 16:
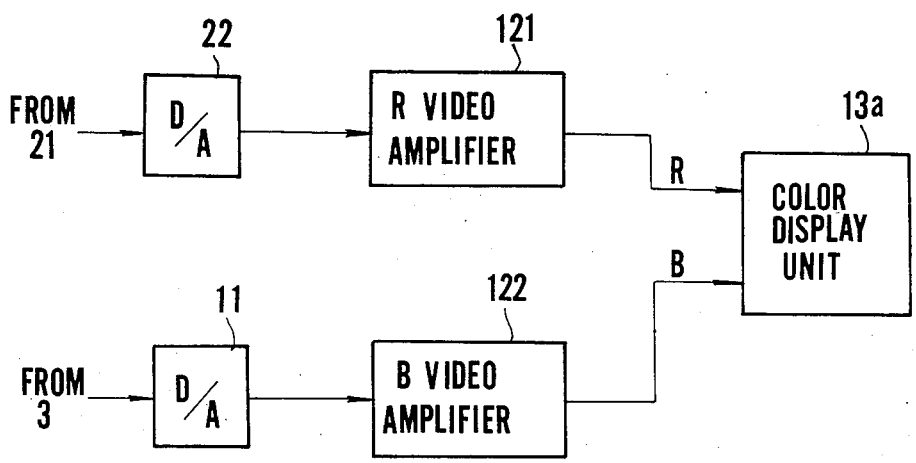

Various methods of effecting the display can be conceived. A first is a method in which the conventional B-mode image and the attenuation distribution image of the present invention are displayed by being switched between on a time-wise basis, a second is a method in which the two images are displayed side by side, and a third is a method in which the two images are displayed in different colors and superimposed. The third method may be practiced by using the arrangement shown in FIG. 16. In this arrangement, the conventional B-mode image is shaded in blue, and the image of the attenuation distribution is shaded in red. Accordingly, the output of a freeze memory 3 in the conventional arrangement is applied as a blue (B) signal to a color display unit 13a such as a color CRT via a video amplifier 122, and the output of the freeze memory 21 is applied as a red (R) signal to the color display unit 13a via a video amplifier 121.

The length of a unit interval for measuring the degree of attenuation can be changed by externally controlling the delay time of the delay circuit 16 by means of the delay time setting unit 25. Specifically, if the delay time is shortened, the unit interval will be shortened to enhance spacial resolution, though only local attenuation degree will be displayed. If the delay time is lengthened, on the other hand, the unit interval is lengthened and spacial resolution deteriorates. In such case, however, mean values of the degree of attenuation of a tissue can be measured. Thus, with such an arrangement, the delay time can be selected depending upon the size of the region of interest to be measured.

Figure 18:
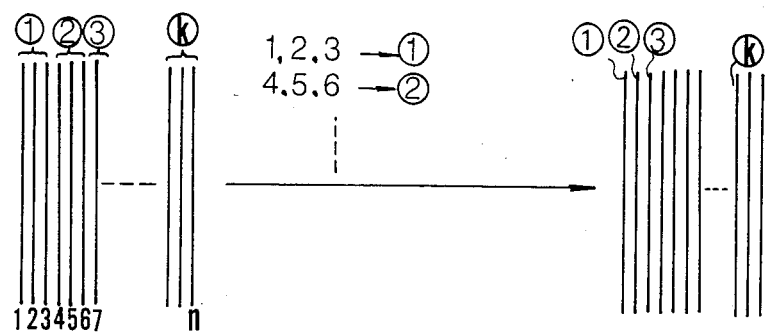
FIGS. 18(a) and (b) are views useful in describing a method of calculating mean values over a number of scanning lines in the embodiment of FIG. 17.
Figure 18:
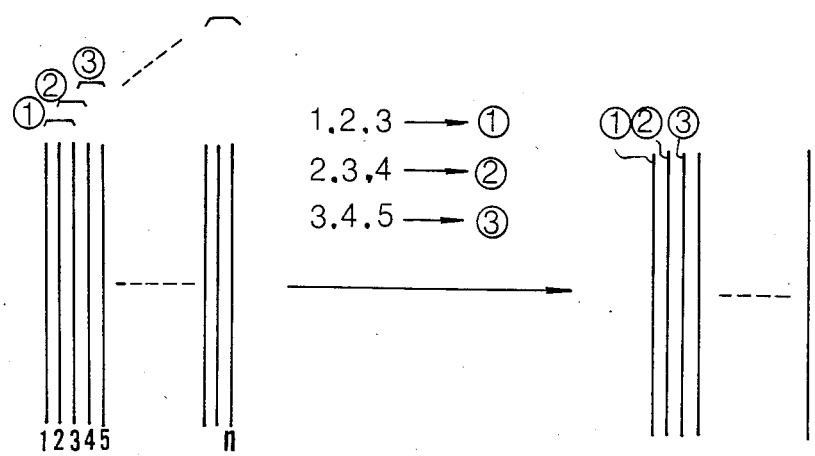

Further, it is possible to average the degree of attenuation along the azimuth, namely in a direction at right angles to the scanning lines. This may be understood from FIGS. 17 and 18(a),(b). In one exemplary arrangement, shown in FIG. 17, the averaging is performed by an arithmetic unit 112 connected to the output side of the freeze memory 21. Specifically, as shown in the left portion of FIG. 18(a), for a plurality of scanning lines 1 through n received from the freeze memory 21, the arithmetic unit 112 is adapted to calculate average values ① through ⓚ of every group of a predetermined number (three in the drawing) of the scanning lines. In other words, as shown in the right portion of FIG. 18(a) the average value ① is the average of scanning lines 1, 2, 3, the average value ② is the average of scanning lines 4, 5, 6, and so on through the last three scanning lines up to k. The calculated average values are displayed by the display unit 13 for each group of the predetermined number of scanning lines. As shown in FIG. 18(b), the averaging operation may be performed by taking the average of scanning lines 1, 2 and 3, then of lines 2, 3 and 4, next of lines 3, 4 and 5, and so on, with each of the scanning lines being included in an average value a predetermined number of times (three in the drawing) in successive fashion to form scanning lines 1, 2, 3 . . . in which a total of n−2 lines are averaged. It is also permissible to externally control by a scanning line setting unit 31 (FIG. 17) the number of scanning lines averaged.

Figure 21:
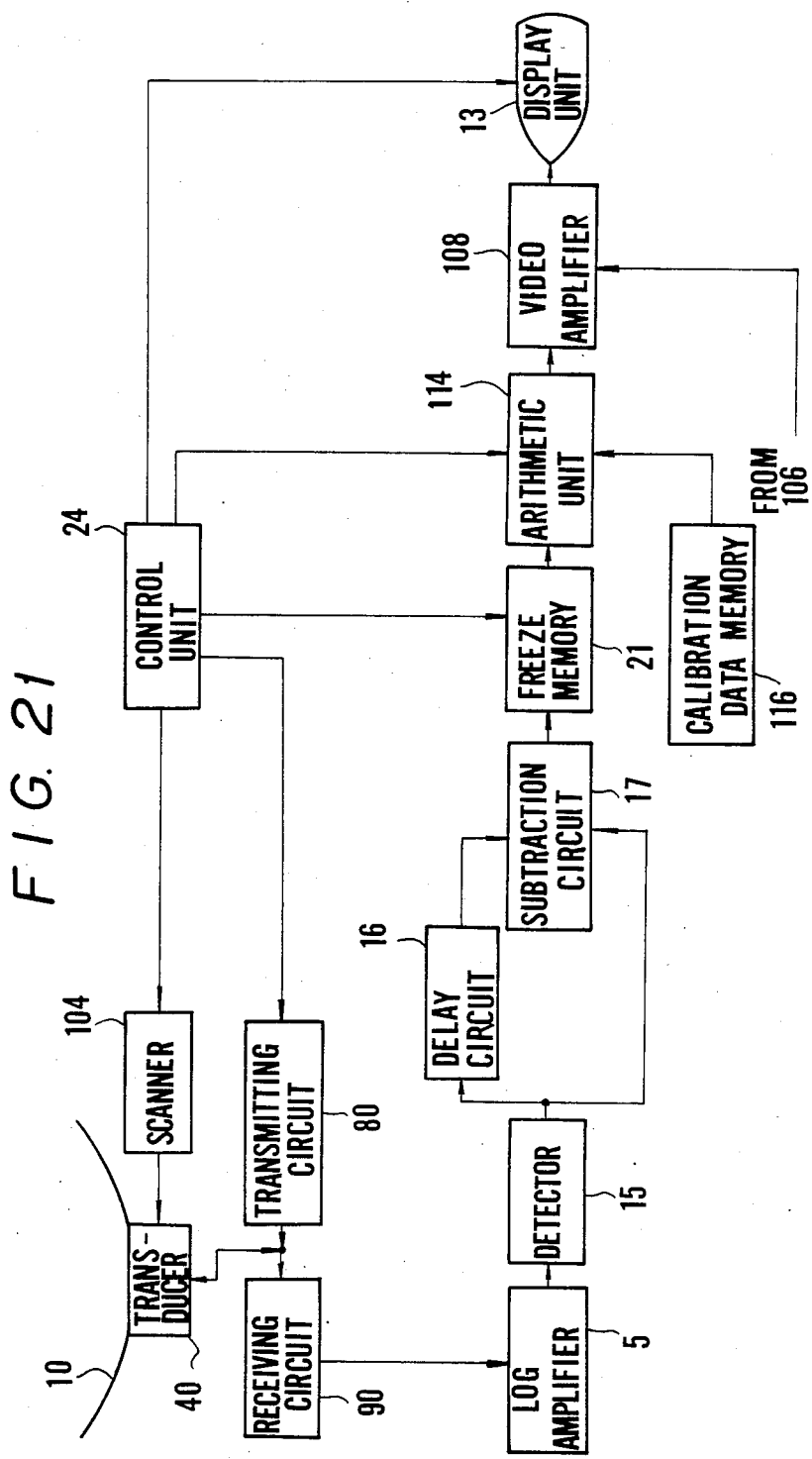

The above-described calibration of the sound field characteristic of transducer 40 is performed by a circuit arrangement shown in FIG. 21 which includes an arithmetic unit 114 for executing a calibration calculation, and a calibration data memory 116 for storing the calibration data described earlier. The arithmetic unit 114 is adapted to perform a calibration operation on the signal from the freeze memory 21 using the calibration data from the calibration data memory 116, and to deliver the resulting signal via video amplifier 108 to the display unit 13 where the signal is displayed. Though a arithmetic circuit for calibration is similarly provided in the block 106 of the apparatus shown in FIG. 14, the circuit is not illustrated.

Figure 23:
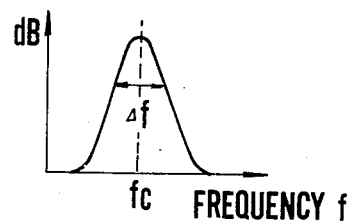
FIGS. 23 and 26 are frequency characteristics useful in describing the embodiments shown in FIGS. 22 and 25 respectively.
Figure 22:
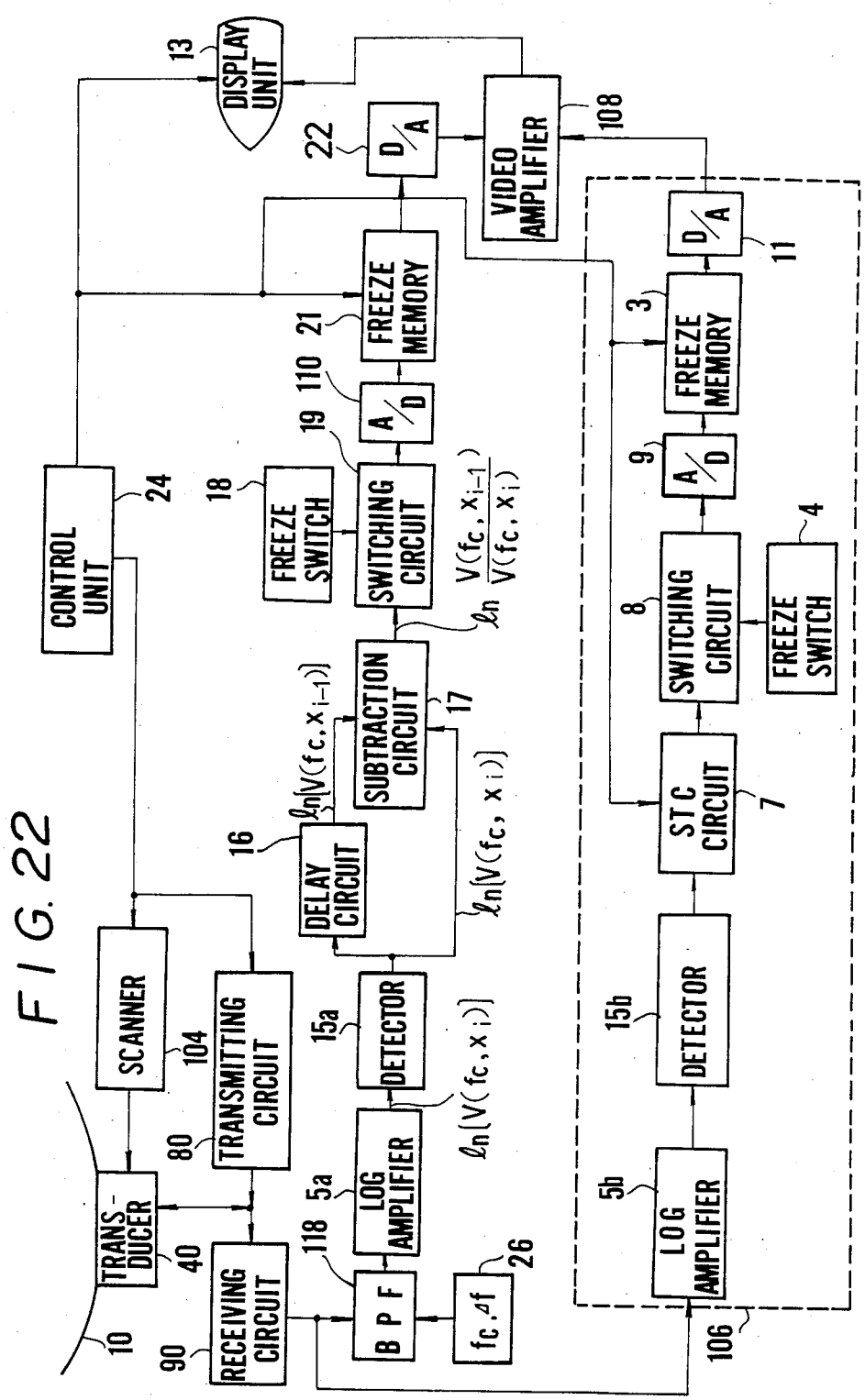

Another embodiment of the present invention will now be described with reference to the block diagram of FIG. 22. This embodiment is distinguishable over that of FIG. 14 in that the output of the receiving circuit 90 is applied to a log amplifier 5a through a band-pass filter 118. If the band-pass filter (BPF) 118 used has a center frequency $f_c$ and a bandwidth $\Delta f$, as shown in FIG. 23, attenuation information relating to frequencies within this frequency band can be measured through a principle similar to that applied in the apparatus of FIG. 14. Attenuation information in a desired frequency band can be measured by externally controlling the frequency bandwidth $\Delta f$ and center frequency $f_c$ through use of a frequency band setting circuit 26. Any of the three display methods described in connection with the embodiment of FIG. 14 can be used.

Figure 24:
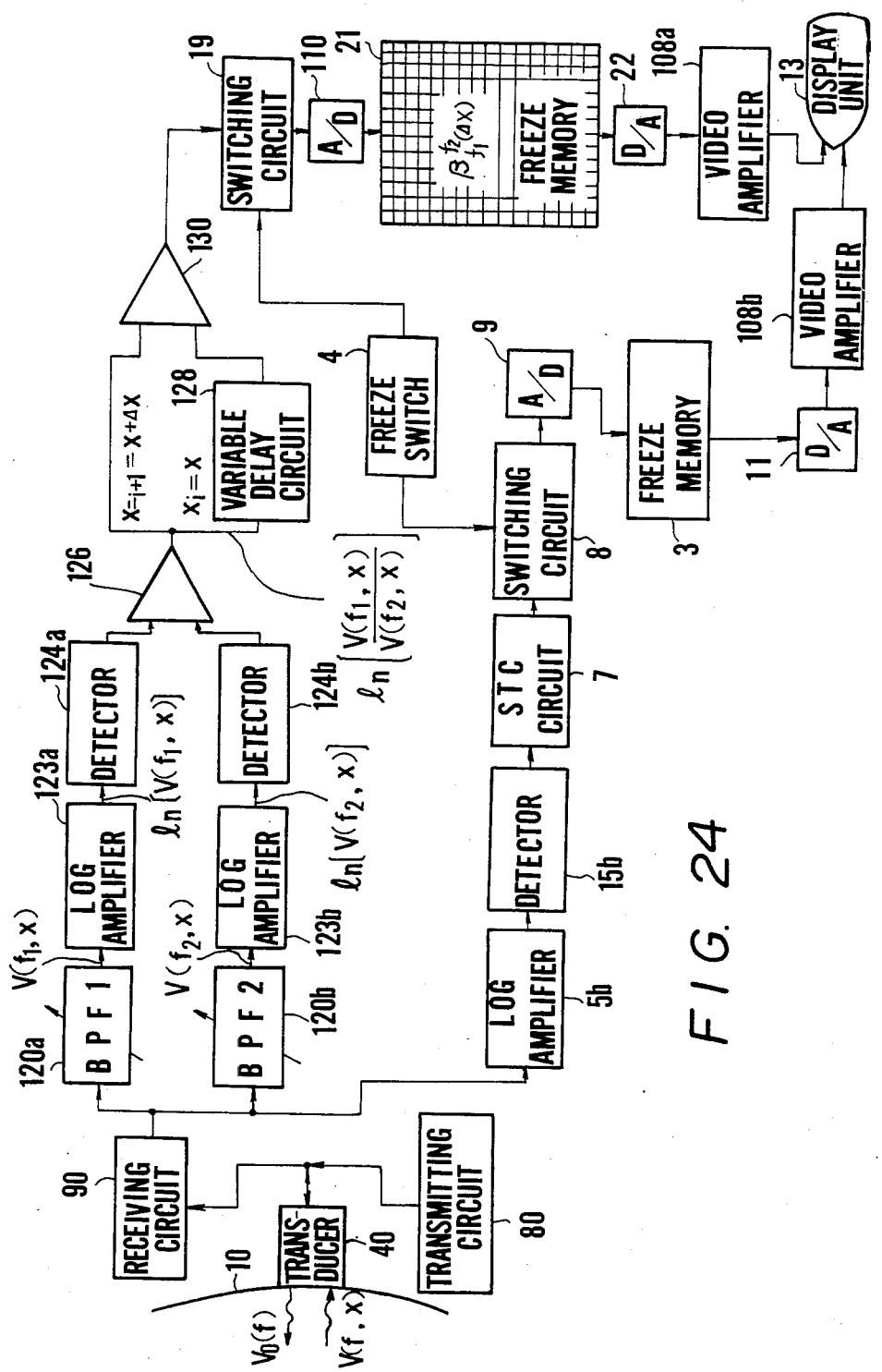

Let us now discuss an embodiment illustrated in FIG. 24, in which information relating to the frequency dependence of attenuation is measured in a manner set forth earlier in the description of the principle of the present invention. Echo signals are separated into two different frequency bands by band-pass filters (BPF1, BPF2) 120a, 120b. The signals from the filters 120a, 120b are applied to a subtraction circuit 126 via log amplifiers 123a, 123b and detectors 124a, 124b, respectively. The subtraction circuit 126 calculates the difference $\ln[V(f_1,x)/V(f_2,x)]$ between signals obtained from the detectors 124a, 124b. Thereafter, signal processing similar to that of the embodiments shown in FIGS. 14 and 22 is executed until the display unit 13 develops the value of $$\beta_{f_1}^{f_2}(\Delta x) = \ln \left[ \frac{V(f_1, x_{i+1})}{V(f_2, x_{i+1})} / \frac{V(f_1, x_i)}{V(f_2, x_i)} \right]$$

as a brightness-modulated tomograph. Any of the three display methods described above in conjunction with the embodiment of FIG. 14 can be used.

Figure 26:
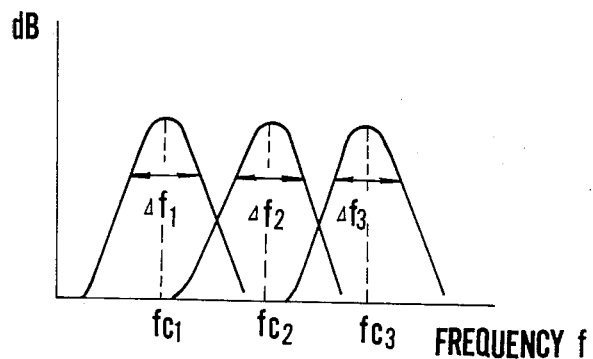

Still another embodiment will now be described with reference to FIG. 25, in which the embodiment of FIG. 24 is provided with a third band-pass filter (BPF3) 120c and an associated logarithmic amplifier 123c and detector 124c. Outputs corresponding to, e.g., three colors of red, blue and green can be obtained on the color display unit 13a, such as color CRT monitor. With this arrangement, therefore, each of the three colors of the tomographs obtained can be correlated with the degree of attenuation in each frequency band and the color of the output will change depending upon the intensity of the color of each component of the three colors. For example, as shown in FIG. 26, assume that three frequencies $f_{c1}$, $f_{c2}$, $f_{c3}$ are set ($f_{c1} < f_{c2} < f_{c3}$) and that the colors corresponding thereto are red, green and blue, respectively. If the frequency band components are the same in such case, then the resulting color of the display will be white. However, if, e.g., blue, which is the color of the high-frequency component ($f_{c3}$), diminishes, then the displayed image will approach the color yellow.

Accordingly, the color which appears on the color display unit 13a accurately reflects the information relating to the frequency dependence of attenuation, and it is possible for an observer to intuitively grasp from the difference in color any change in tissue characteristic. Further, if it is arranged so that the three frequency bands ($f_c$, $\Delta f$) can be varied independently as in the embodiment of FIG. 24, then it will be possible to obtain a "Spectra Color" tomograph based on a combination of desired frequency bands. Any of the three display methods described above in conjunction with the embodiment of FIG. 14 can be used.

An embodiment shown in FIG. 27 expands upon the embodiment of FIG. 25. The echo signals are separated into three frequency bands $f_{c1}$, $f_{c2}$, $f_{c3}$, and the differences between $f_{c1}$ and $f_{c2}$, $f_{c2}$ and $f_{c3}$, $f_{c3}$ and $f_{c1}$ are calculated. This makes it possible to simultaneously obtain three sets of information relating to the frequency dependence of attenuation. This embodiment is similar to that of FIG. 25 in other aspects. For example, correspondence between the three sets of attenuation information and the colors red, green and blue is established and the information is then displayed as a tomograph on the color display unit 13a. If the three frequency bands ($f_c$, $\Delta f$) are rendered independently variable, as mentioned in connection with FIG. 25, then a "Spectra Color" tomograph based on a combination of desired frequency bands can be obtained.

Figure 28:
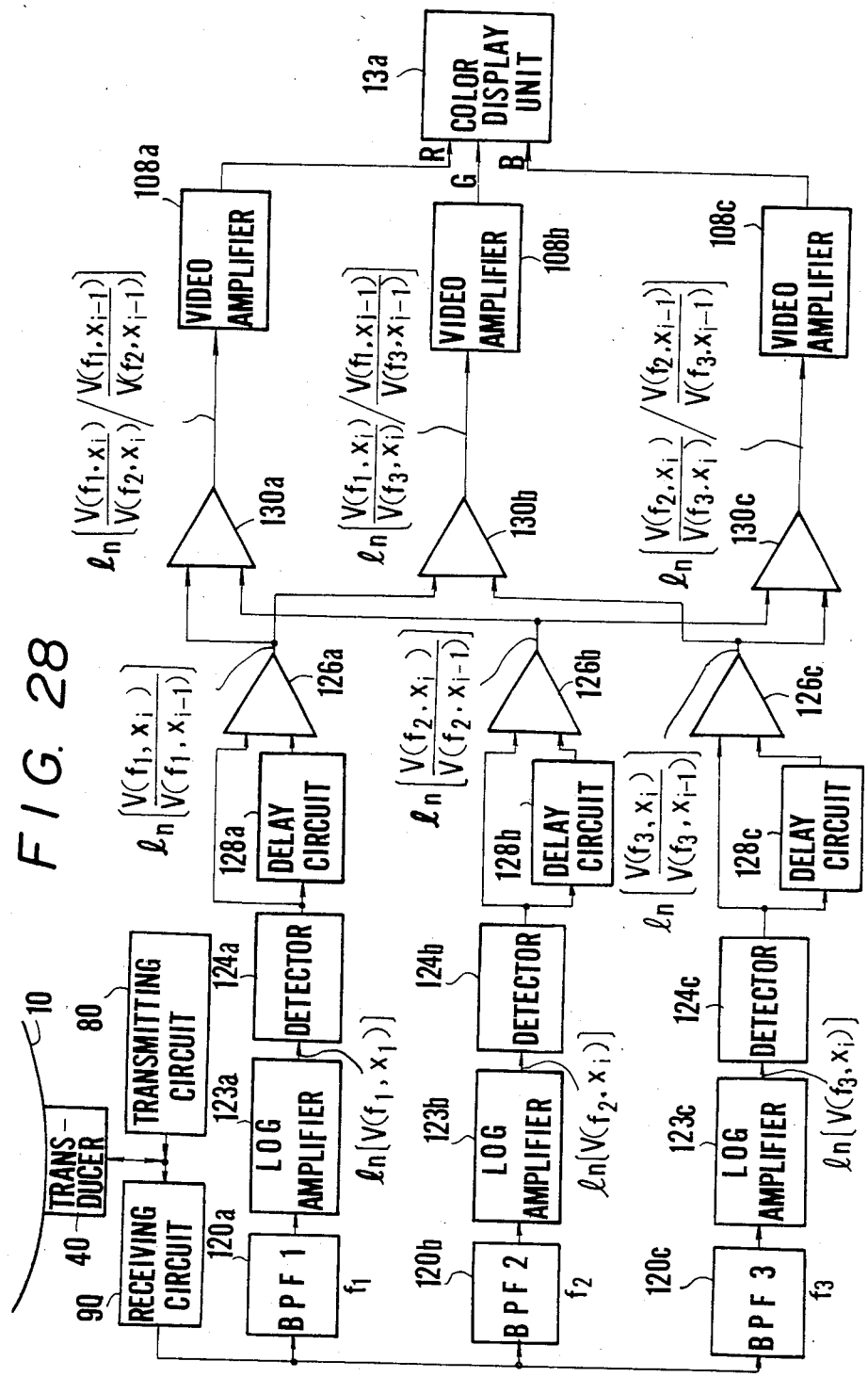

An embodiment shown in FIG. 28 is similar to that of FIG. 27 but calculates the frequency band differences at the input stage to the video amplifiers 108a through 108c. Any of the three display methods described above in conjunction with the embodiment of FIG. 14 can be used.

Figure 29:
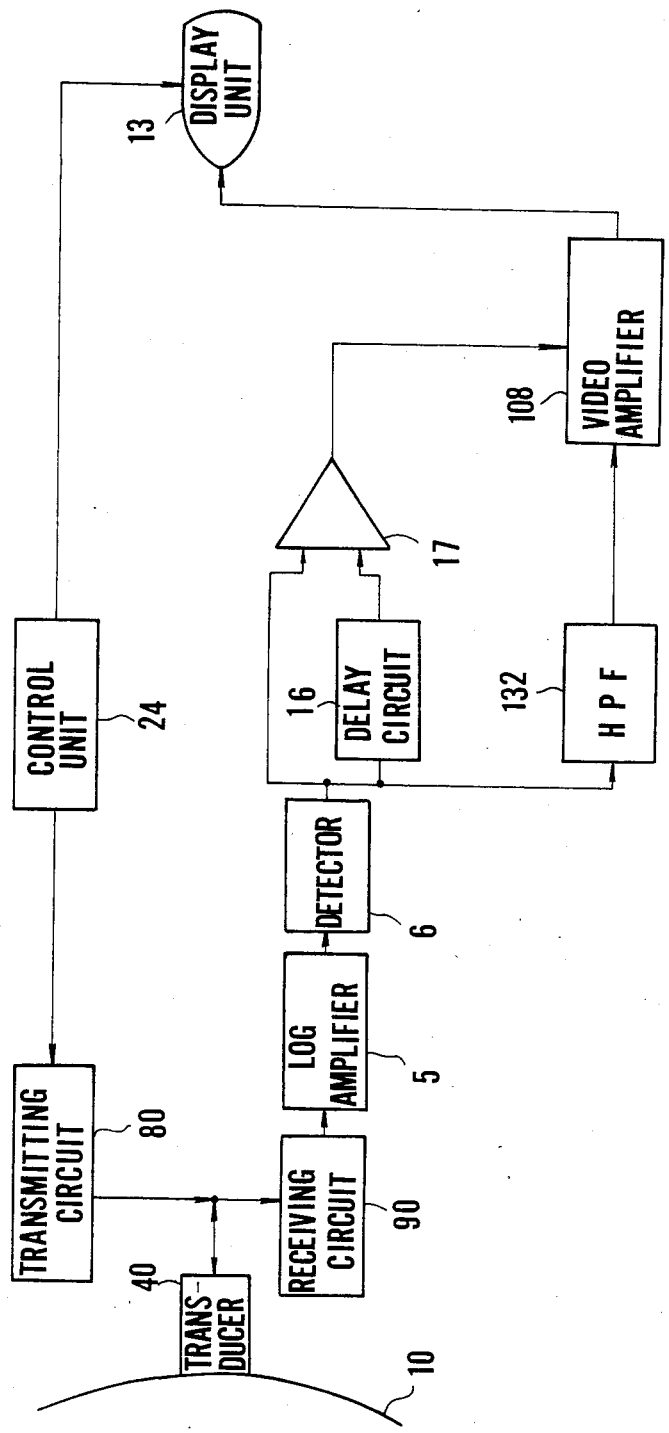

A further embodiment of the present invention is illustrated in FIG. 29. Here a drive signal transmitted by the transmitting circuit 80 causes the transducer 40 to emit an ultrasonic pulse toward the object 10. The echo signal is received by the transducer 40 and directed through the receiving circuit 90, log amplifier 5 and detector 6. As in the embodiment of FIG. 4, the resulting signal is applied to the delay circuit 16 and substraction circuit 17 so that the degree of attenuation may be measured. The resulting difference signal is applied to the video amplifier 108 for display on the display unit 13 as an image of the attenuation distribution.

Meanwhile, the output of the detector 6 is also applied to a high-pass filter (HPF) 132, which removes frequencies in the lower region of the frequency band, thereby emphasizing the high-frequency echo signal, namely the echo component of the tissue boundary, in relative terms. The resulting signal is applied to the video amplifier 108 for display on the display unit 13 as an enhanced image of the echo at the tissue boundary.

It should be noted that a tomograph developed simultaneously in terms of attenuation and echo enhancement can be obtained by mixing the two images at the video amplifier 108 and then displaying them in superimposed form.

The present invention is not limited to the embodiments described hereinabove. In other possible modifications a plurality of band-pass filters can be provided and attenuation information relating to a plurality of corresponding frequency bands measured to further enhance resolution with respect to frequency. Plural sets of frequency difference information can also be measured. Further, the single transducer can be replaced by an array of transducers to make possible a developed display of a real-time "Spectra Color" tomograph by performing linear and sector electronic scanning.

It should be obvious from the description of the foregoing embodiments that the present invention features the important advantage of high-speed signal processing by comparatively simple analog circuitry and is therefore applicable to real-time processing.

CONCRETE EFFECTS OF THE INVENTION

According to the present invention as described above, a distribution of attenuation of ultrasonic waves caused by absorption, reflection and scattering of the ultrasonic waves in an object under measurement, particularly biological tissue, as well as a distribution of the frequency dependence of the degree of attenuation, can be developed and displayed as a tomograph, on the basis of which these characteristics can be intuitively grasped. Furthermore, the degree of attenuation in desired frequency bands can be displayed as a so-called "Spectra Color" image without the measurement system or the structure of the object under measurement having any influence upon the color of the obtained tomograph, unlike the prior-art arrangements. The invention thus provides a method and apparatus for obtaining a real-time "Spectra Color" tomograph wherein an accurate correlation is established between tomograph color and the information indicative of attenuation in the object.

As many apparently widely different embodiments of the present invention can be made without departing from the spirit and scope thereof, it is to be understood that the invention is not limited to the specific embodiments thereof except as defined in the appended claims.

What we claim is:

1. An ultrasonic measurement apparatus for measuring an attenuation degree of an object under examination, comprising:
    ultrasonic transceiving means for transmitting ultrasonic pulses into the object and receiving an ultrasonic echo signal, reflected from within the object,
    band pass filter means coupled to the ultrasonic transceiving means for passing a component of said ultrasonic echo signal within a frequency band,
    delay means coupled to the band pass filter means for delaying said component of the ultrasonic echo signal by a time corresponding to the length of a unit distance through the object for defining the attenuation degree of the object,
    calculating means coupled to the band pass filter means and the delay means for calculating the attenuation degree on the basis of a ratio of intensities of the component passed by the band pass filter means and the component delayed by the delay means; and -
    display means connected to said calculating means for displaying the calculated attenuation degree as a brightness modulated visible image.

2. The ultrasonic measurement apparatus according to claim 1, wherein said ultrasonic transceiving means comprises: transmitting means for transmitting an ultrasonic pulse into the object over a relatively wide band.

3. The ultrasonic measurement apparatus according to claim 1, comprising horizontal scanning means for scanning the ultrasonic transceiving means to receive a plurality of ultrasonic echo signals, and said calculating means has means for calculating mean attenuation degree over predetermined numbers of said plurality of ultrasonic echo signals.

4. The ultrasonic measurement apparatus according to claim 1, wherein said band pass filter means comprises a plurality of band pass circuits each of which possesses a unique frequency band,
said calculating means calculates a plurality of attenuation degrees each of which corresponds to said each unique frequency band respectively, and
said display means comprises a color image circuit in which a primary color corresponds to the unique frequency band.

5. The ultrasonic measurement apparatus according to claim 1, comprising high pass filter means coupled to the ultrasonic transceiving means for passing a high-frequency component of the ultrasonic echo signal, and adding means for adding the attenuation degree calculated by the calculating means to said high-frequency component.

6. An ultrasonic measurement apparatus for measuring an attenuation degree of an object under examination, comprising:
ultrasonic transceiving means for transmitting an ultrasonic pulse into the object and receiving an ultrasonic echo signal, reflected from within the object,
first band pass filter means coupled to the transceiving means for passing a first component of said ultrasonic echo signal within a first frequency band,
second band pass filter means coupled to the transceiving means for passing a second component of said ultrasonic echo signal within a second frequency band,
first calculating means coupled to the first and the second band pass filter means for calculating a first ratio from said first and said second component and producing a corresponding first ratio signal,
delay means coupled to the first calculating means for delaying said first ratio signal by a time corresponding to the length of a unit distance through the object for defining the attenuation degree of the object,
second calculating means coupled to the first calculating means and the delay means for calculating the attenuation degree on the basis of a ratio of said first ratio signal and the delayed first ratio signal; and
display means coupled to the second calculating means for displaying the calculated attenuation degree as a brightness modulated visible image.

7. The ultrasonic measurement apparatus according to claim 6, wherein said ultrasonic transceiving means comprises transmitting means for transmitting an ultrasonic pulse into the object over a relatively wide band.

8. The ultrasonic measurement apparatus according to claim 6, comprising horizontal scanning means for scanning the ultrasonic transceiving means to receive a plurality of ultrasonic echo signals, and said calculating means has means for calculating mean attenuation degree over predetermined numbers of said plurality of ultrasonic echo signals.

9. The ultrasonic measurement apparatus according to claim 6, wherein said band pass filter means comprises a plurality of band pass circuits each of which possesses a unique frequency band,
said calculating means calculates a plurality of attenuation degrees each of which corresponds to said each unique frequency band respectively, and
said display means comprises a color image circuit in which a primary color corresponds to the unique frequency band.

10. The ultrasonic measurement apparatus according to claim 6, comprising high-pass filter means coupled to the ultrasonic transceiving means for passing a high-frequency component of the ultrasonic echo signal, and adding means for adding the attenuation degree calculated by the calculating means to said high-frequency component.

11. An ultrasonic measurement apparatus for measuring an attenuation degree of an object under examination, comprising:
ultrasonic transceiving means for transmitting an ultrasonic pulse into the object and receiving an ultrasonic echo signal, reflected from within said object,
delay means coupled to the ultrasonic transceiving means for delaying said ultrasonic echo signal by a time corresponding to the length of a unit distance through the object for defining the attenuation degree of the object,
calculating means coupled to the delay means and the ultrasonic transceiving means for calculating the attenuation degree on the basis of a ratio of intensities of the received ultrasonic echo signal and the ultrasonic echo signal as delayed by the delay means; and
display means coupled to the calculating means for displaying the calculated attenuation degree as a brightness modulated visible image.

12. The ultrasonic measurement apparatus according to claim 11, comprising horizontal scanning means for scanning the ultrasonic transceiving means to receive a plurality of ultrasonic echo signals, and said calculating means includes means for calculating mean attenuation degree over predetermined numbers of said plurality of ultrasonic echo signals.

* * * * *

UNITED STATES PATENT AND TRADEMARK OFFICE
CERTIFICATE OF CORRECTION

PATENT NO. : 4,646,748
DATED : March 3, 1987
INVENTOR(S) : Tadashi FUJII et al

It is certified that error appears in the above-identified patent and that said Letters Patent is hereby corrected as shown below:

Column 7, in the second listed formula "+" should read -- = --;

Column 7, line 38, "to to" should read -- to --;

Column 17, line 41, "FIG. 4" should read -- FIG. 14 --.

Signed and Sealed this

Fifteenth Day of March, 1988

Attest:

DONALD J. QUIGG

*Attesting Officer*   Commissioner of Patents and Trademarks